US010757988B1

(12) United States Patent
Swogger et al.

(10) Patent No.: US 10,757,988 B1
(45) Date of Patent: Sep. 1, 2020

(54) PERSONAL PROTECTIVE EQUIPMENT WITH FUNCTIONALIZED NANOTUBE COMPOSITIONS TO CONTROL PATHOGENS SUCH AS SARS COV-2 (CORONAVIRUS)

(71) Applicant: MOLECULAR REBAR DESIGN, LLC, Austin, TX (US)

(72) Inventors: Kurt W. Swogger, Austin, TX (US); Gregory L. Porter, Spring, TX (US); Milos Marinkovic, Austin, TX (US)

(73) Assignee: Molecular Rebar Design, LLC, Austin, TX (US)

( * ) Notice: Subject to any disclaimer, the term of this patent is extended or adjusted under 35 U.S.C. 154(b) by 0 days.

(21) Appl. No.: 16/871,994

(22) Filed: May 11, 2020

Related U.S. Application Data

(60) Provisional application No. 63/006,486, filed on Apr. 7, 2020, provisional application No. 63/012,311, filed on Apr. 20, 2020.

(51) Int. Cl.
| | |
|---|---|
| *A41D 13/11* | (2006.01) |
| *D01F 9/12* | (2006.01) |
| *A61M 16/06* | (2006.01) |
| *B82Y 30/00* | (2011.01) |
| *A61M 16/10* | (2006.01) |

(52) U.S. Cl.
CPC ......... *A41D 13/1192* (2013.01); *A61M 16/06* (2013.01); *A61M 16/1065* (2014.02); *D01F 9/12* (2013.01); *A61M 2202/0488* (2013.01); *A61M 2202/203* (2013.01); *A61M 2202/206* (2013.01); *A61M 2205/0205* (2013.01); *B82Y 30/00* (2013.01)

(58) Field of Classification Search
CPC .... A41D 13/11; A41D 13/1192; A41D 31/30; A41D 31/305; A62B 23/00; A62B 23/02; A62B 23/025; A62B 23/06; A62B 18/00; A62B 18/02; A62B 18/025; A61M 16/06; A61M 2202/20; A61M 2202/203; A61M 2202/206; A61M 2205/0205; B82Y 30/00; C01B 32/158; C01B 32/159; C01B 32/16; C01B 32/168; D01F 9/12
See application file for complete search history.

(56) References Cited

U.S. PATENT DOCUMENTS

| | | | | |
|---|---|---|---|---|
| 4,856,509 A | * | 8/1989 | Lemelson | A41D 13/1146 128/206.19 |
| 2009/0130161 A1 | * | 5/2009 | Sarangapani | A01N 59/20 424/409 |
| 2010/0098877 A1 | * | 4/2010 | Cooper | B01D 53/228 427/551 |
| 2013/0137324 A1 | * | 5/2013 | Tang | C09D 5/006 442/131 |
| 2015/0040920 A1 | * | 2/2015 | Spanner | B32B 5/00 128/863 |
| 2015/0238476 A1 | * | 8/2015 | Bosnyak | A61K 31/455 424/400 |
| 2016/0016022 A1 | * | 1/2016 | Qian | A41D 13/1192 128/206.12 |
| 2016/0106098 A1 | * | 4/2016 | Worley | A01N 59/16 424/404 |
| 2017/0291818 A1 | * | 10/2017 | Swogger | C12N 5/0623 |
| 2017/0292063 A1 | * | 10/2017 | Sturtevant | C01B 32/174 |
| 2018/0037459 A1 | * | 2/2018 | Swogger | A61K 31/455 |
| 2018/0298221 A1 | * | 10/2018 | Swogger | C09D 11/106 |
| 2018/0311515 A1 | * | 11/2018 | Wilson | A62B 9/006 |
| 2019/0110382 A1 | * | 4/2019 | Bosnyak | C01B 32/178 |
| 2019/0144281 A1 | * | 5/2019 | Peddini | C01B 32/174 524/525 |
| 2019/0177497 A1 | * | 6/2019 | Peddini | C01B 32/174 |

FOREIGN PATENT DOCUMENTS

KR         20130011193 A   *   1/2013

OTHER PUBLICATIONS

Machine translation of KR-20130011193-A.*

* cited by examiner

*Primary Examiner* — Joseph D. Boecker
(74) *Attorney, Agent, or Firm* — Stephen P. Krupp

(57) ABSTRACT

Nanotube compositions may be employed in many different forms alone, and/or with surfactants, with antiviral metals, with antigens, and/or with various drugs to control pathogens like viruses e.g., SARS COVID-2, bacteria, mold, fungi, chemical or biological agents etc in masks or other personal protection equipment. The personal protection equipment such as masks reduce, control, absorb, deactivate, detoxify, and/or kill the pathogens such that a pathogen or pathogens deleterious effects are reduced and/or eliminated to a user of the mask.

19 Claims, 3 Drawing Sheets

Figure 1:
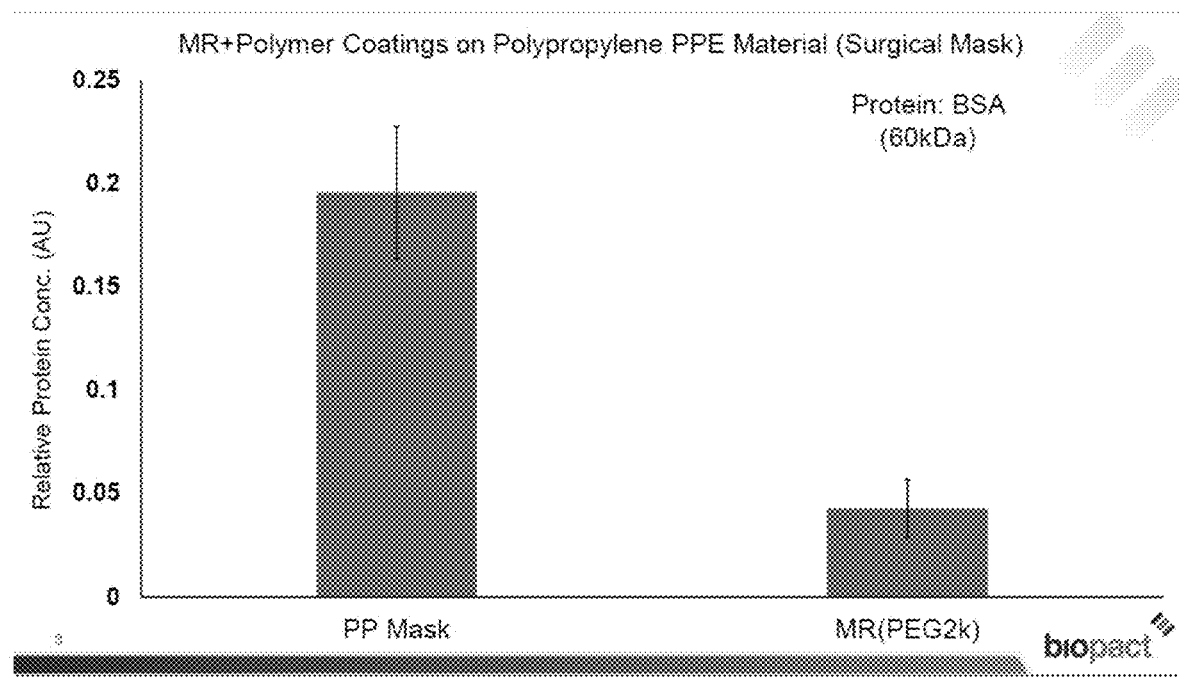

Protein Filtering by Varying MR(PVA) Coating Densities (Constant 1:0.45 MR:PVA Ratio) on Polypropylene PPE Material (Surgical Mask)

Protein Filtering on PP Filters, at Constant Ratios of MR to PVA or PVP

Protein Filtering on PP Filters, Adjusting MR(PVP) Ratio; at Constant MR Concentration

PERSONAL PROTECTIVE EQUIPMENT WITH FUNCTIONALIZED NANOTUBE COMPOSITIONS TO CONTROL PATHOGENS SUCH AS SARS COV-2 (CORONAVIRUS)

CROSS REFERENCE TO RELATED APPLICATIONS

This application claims priority to U.S. provisional application Nos. 63/006,486 filed on Apr. 7, 2020 and 63/012,311 filed Apr. 20, 2020. This application is related to U.S. Pat. Nos. 10,414,656, 4,842,922, 4,644,045; U.S. Ser. No. 13/164,456, filed Jun. 20, 2011, and its progeny; and U.S. Ser. No. 13/140,029, filed Aug. 9, 2011, and its progeny, the disclosures of each of which is incorporated herein by reference.

FIELD OF INVENTION

The present invention is directed to filtration fabrics comprising novel discrete carbon nanotube compositions having targeted oxidation levels and/or content, and formulations thereof, such as with surfactants. Such fabrics can be woven or nonwoven and are especially useful in filtering and trapping proteins, viruses and the like. The fabrics are especially useful in personal protective equipment such as masks worn around the nose and mouth.

BACKGROUND AND SUMMARY OF THE INVENTION

Carbon nanotubes can be classified by the number of walls in the tube, single-wall, double wall and multiwall. Carbon nanotubes are currently manufactured as agglomerated nanotube balls, bundles or forests attached to substrates. Use of carbon nanotubes as a reinforcing agent in elastomeric, thermoplastic or thermoset polymer composites is an area in which carbon nanotubes are predicted to have significant utility. However, utilization of carbon nanotubes in these applications has been hampered due to the general inability to reliably produce individualized carbon nanotubes and the ability to disperse the individualized carbon nanotubes in a polymer matrix. Bosnyak et al., in various patent applications (e.g., US 2012-0183770 A1 and US 2011-0294013 A1), have made discrete carbon nanotubes through judicious and substantially simultaneous use of oxidation and shear forces, thereby oxidizing both the inner and outer surface of the nanotubes, typically to approximately the same oxidation level on the inner and outer surfaces, resulting in individual or discrete tubes.

The present invention differs from those earlier Bosnyak et al. applications and disclosures. The present invention describes a composition of discrete, individualized carbon nanotubes having targeted, or selective, oxidation levels and/or content on the exterior and/or interior of the tube walls. Such novel carbon nanotubes can have little to no inner tube surface oxidation, or differing amounts and/or types of oxidation between the tubes' inner and outer surfaces. These new discrete tubes are useful in many applications, including such chemical such as Surfactants, which can then be used as an additive in compounding and formulation of elastomeric, thermoplastic and thermoset composite for improvement of mechanical, electrical and thermal properties.

One embodiment of the present invention is a woven or nonwoven fabric, each comprising at least one layer having at least one surface, wherein the at least one layer comprises a composition comprising a plurality of discrete carbon nanotubes, wherein the discrete carbon nanotubes comprise an interior and exterior surface, the interior surface comprising an interior surface oxidized species content and the exterior surface comprising an exterior surface oxidized species content, wherein the interior surface oxidized species content differs from the exterior surface oxidized species content by at least 20%, and as high as 100%. Preferably, the nonwoven fabric comprises at least one member from the group consisting of spunbonded fabric, thermally bonded staple fiber, spunlaced fabric, and melt blown fabric.

The fabric can comprise at least one thermoplastic polymer selected from the group consisting of polypropylene, polyethylene, polyethylene terephthalate, and nylon. Preferably, the spunbonded fabric comprises at least two layers. Each layer of the spunbonded fabric preferably comprises polypropylene.

The plurality of discrete carbon nanotubes in the spunbonded fabric preferably has a surfactant in contact with at least a portion of a surface of the nanotubes, especially when the surfactant comprises polyvinyl alcohol in contact with at least a portion of a surface of the nanotubes.

The spunbonded fabric is especially preferred comprising at least 3 layers.

The spunbonded fabric of claim 8 wherein the at least one layer comprises at least one interior layer of the fabric, but the nanotubes only contact an interior layer.

Other embodiments include a filtration mask comprising the spunbonded fabric, a wipe comprising the fabrics, a filter comprising the spunbonded fabric.

Another embodiment is a method of filtering SARS CoV-2 comprising contacting the SARS CoV-2 with the mask disclosed herein especially wherein the interior layer of the fabric is coated with the nanotube composition using a coating technique such as spraying.

The plurality of discrete carbon nanotubes can comprise a plurality of open-ended tubes, and/or wherein the interior surface oxidized species content is less than the exterior surface oxidized species content, the composition comprising a plurality of discrete carbon nanotubes, wherein the discrete carbon nanotubes comprise an interior and exterior surface, each surface comprising an interior surface oxidized species content and an exterior surface oxidized species content, wherein the interior surface oxidized species content differs from the exterior surface oxidized species content by at least 20%, and as high as 100%, preferably wherein the interior surface oxidized species content is less than the exterior surface oxidized species content.

The interior surface oxidized species content can be up to 3 weight percent relative to carbon nanotube weight, preferably from about 0.01 to about 3 weight percent relative to carbon nanotube weight, more preferably from about 0.01 to about 2, most preferably from about 0.01 to about 1. Especially preferred interior surface oxidized species content is from zero to about 0.01 weight percent relative to carbon nanotube weight.

The exterior surface oxidized species content can be from about 1 to about 6 weight percent relative to carbon nanotube weight, preferably from about 1 to about 4, more preferably from about 1 to about 2 weight percent relative to carbon nanotube weight. This is determined by comparing the exterior oxidized species content for a given plurality of nanotubes against the total weight of that plurality of nanotubes.

The interior and exterior surface oxidized species content totals can be from about 1 to about 9 weight percent relative to carbon nanotube weight, or from about 1 to about 7 weight percent relative to carbon nanotube weight, or from about 1 to about 5 weight percent relative to carbon nanotube weight, or from about 1 to about 3 weight percent relative to carbon nanotube weight, or from about 0.5 to about 1.5 weight percent relative to carbon nanotube weight.

Another embodiment of the invention is a composition comprising a plurality of discrete carbon nanotubes, wherein the discrete carbon nanotubes comprise an interior and exterior surface, each surface comprising an interior surface and an exterior surface oxidized species content, wherein the interior surface oxidized species content comprises from about 0.01 to less than about 1 percent relative to carbon nanotube weight and the exterior surface oxidized species content comprises more than about 1 to about 3 percent relative to carbon nanotube weight.

The discrete carbon nanotubes of either composition embodiment above preferably comprise a plurality of open-ended tubes, more preferably the plurality of discrete carbon nanotubes comprise a plurality of open-ended tubes. The discrete carbon nanotubes of either composition embodiment above are especially preferred wherein the inner and outer surface oxidation difference is at least about 0.2 weight percent.

The compositions described herein can be used as an ion transport. Various species or classes of compounds/drugs/chemicals which demonstrate this ion transport effect can be used, including ionic, some non-ionic compounds, hydrophobic or hydrophilic compounds.

The new carbon nanotubes disclosed herein are also useful in ground water remediation.

The compositions comprising the novel discrete targeted oxidized carbon nanotubes and also be used as a component in, or as, a sensor.

The compositions disclosed herein can also be used as a component in, or as, drug delivery or controlled release formulations.

In some embodiments, the compositions disclosed herein can be used as a component in, or as, payload molecule delivery or drug delivery or controlled release formulations. In particular various drugs, including small molecule therapeutics, peptides, nucleic acids, or combinations thereof may be loaded onto nanotubes and delivered to specific locations. Discrete carbon nanotubes may be used to help small molecules/peptides/nucleic acids that are cell membrane impermeable or otherwise have difficulty crossing the cell membrane to pass through the cell membrane into the interior of a cell. Once the small molecule/peptide/nucleic acid has crossed the cell membrane, it may become significantly more effective. Small molecules are defined herein as having a molecular weight of about 500 Daltons or less.

The pro-apoptotic peptide KLAKLAK is known to be cell membrane impermeable. By loading the peptide onto discrete carbon nanotubes KLAKLAK is able to cross the cell membrane of LNCaP human prostate cancer cells and trigger apoptosis. The KLAKLAK-discrete carbon nanotube construct can lead to the apoptosis of up to 100% of targeted LNCaP human prostate cancer cells. Discrete carbon nanotubes may also be useful for delivering other small molecules/peptides/nucleic acids across the cell membranes of a wide variety of other cell types. Discrete carbon nanotubes may be arranged to have a high loading efficiency, thereby enabling the delivery of higher quantities of drugs or peptides. In some instances, this transport across the cell membrane may be accomplished without the need for targeting or permeation moieties to aid or enable the transport. In other instances, the discrete carbon nanotubes may be conjugated with a targeting moiety (ex. peptide, chemical ligand, antibody) in order to assist with the direction of a drug or small molecule/peptide/nucleic acid towards a specific target. Discrete carbon nanotubes alone are well tolerated and do not independently trigger apoptosis.

Peptides, small molecules, and nucleic acids and other drugs may be attached to the exterior of the discrete carbon nanotubes via Van der Waals, ionic, or covalent bonding. As discussed, the level of oxidation may be controlled in order to promote a specific interaction for a given drug or small molecule/peptide/nucleic acid. In some instances, drugs or peptides that are sufficiently small may localize to the interior of discrete carbon nanotubes. The process for filling the interior or discrete carbon nanotubes may take place at many temperatures, including at or below room temperature. In some instances, the discrete carbon nanotubes may be filled to capacity in as little as 60 minutes with both small and large molecule drugs.

The payload molecule can be selected from the group consisting of a drug molecule, a radiotracer molecule, a radiotherapy molecule, diagnostic imaging molecule, fluorescent tracer molecule, a protein molecule, and combinations thereof.

Exemplary types of payload molecules that may be covalently or non-covalently associated with the discrete functionalized carbon nanotubes disclosed herein may include, but are not limited to, proton pump inhibitors, H2-receptor antagonists, cytoprotectants, prostaglandin analogues, beta blockers, calcium channel blockers, diuretics, cardiac glycosides, antiarrhythmics, antianginals, vasoconstrictors, vasodilators, ACE inhibitors, angiotensin receptor blockers, alpha blockers, anticoagulants, antiplatelet drugs, fibrinolytics, hypolipidemic agents, statins, hypnotics, antipsychotics, antidepressants, monoamine oxidase inhibitors, selective serotonin reuptake inhibitor, antiemetics, anticonvulsants, anxiolytic, barbiturates, stimulants, amphetamines, benzodiazepines, dopamine antagonists, antihistamines, cholinergics, anticholinergics, emetics, cannabinoids, 5-HT antagonists, NSAIDs, opioids, bronchodilator, antiallergics, mucolytics, corticosteroids, beta-receptor antagonists, anti cholinergics, steroids, androgens, antiandrogens, growth hormones, thyroid hormones, anti-thyroid drugs, vasopressin analogues, antibiotics, antifungals, antituberculous drugs, antimalarials, antiviral drugs, antiprotozoal drugs, radioprotectants, chemotherapy drugs, cytostatic drugs, and cytotoxic drugs such as paclitaxel.

Batteries comprising the compositions disclosed herein are also useful. Such batteries include lithium, nickel cadmium, or lead acid types.

Formulations comprising the compositions disclosed herein can further comprise an epoxy, a polyurethane, or an elastomer. Such formulations can be in the form of a dispersion. The formulations can also include nanoplate structures.

The compositions can further comprise at least one hydrophobic material in contact with at least one interior surface.

The present invention relates to a composition comprising a plurality of discrete carbon nanotubes and wherein the carbon nanotubes are functionalized with oxygen species on their outermost wall surface. The discrete carbon nanotubes comprise an interior and exterior surface, each surface comprising an interior surface and exterior surface oxidized species content wherein the interior surface oxidized species content comprises from about 0.01 to less than about 1 percent relative to carbon nanotube weight and the exterior surface oxidized species content comprises more than about 1 to about 3 percent relative to carbon nanotube weight and a surfactant wherein the discrete carbon nanotubes have an aspect ratio of 10 to about 500. In some embodiments at least a portion of the discrete carbon nanotube fibers are open ended, preferably wherein 40% to 90% by number of the carbon nanotubes have an aspect ratio of 30-70, and more preferably aspect ratio of 40-60, and 1% to 30% by number of aspect ratio 80-140, most preferably an aspect ratio of 90 to 120. In statistics, a bimodal distribution is a continuous probability distribution with two different modes. These appear as distinct peaks (local maxima) in the probability density function. More generally, a multimodal distribution is a continuous probability distribution with two or more modes. The discrete carbon nanotubes can have a unimodal, bimodal or multimodal distribution of diameters and/or lengths. For example, the discrete carbon nanotubes can have a bimodal distribution of diameters wherein one of the peak values of diameter is in the range 2 to 7 nanometers and the other peak value is in the range 10 to 40 nanometers. Likewise, the lengths of the discrete carbon nanotubes can have a bimodal distribution such that one peak has a maximum value in the range of 150 to 800 nanometers and the second peak has a maximum value in the range 1000 to 3000 nanometers.

The oxygen species can comprise carboxylic acids, phenols, or combinations thereof.

The composition can further comprise a surfactant selected from the group consisting of Surfactants as used herein include compounds that lower the surface tension (or interfacial tension) between two liquids, between a gas and a liquid, or between a liquid and a solid. Surfactants may act as detergents, wetting agents, emulsifiers, foaming agents, and dispersants. Suitable surfactants may include, for example, bio-compatible surfactants selected from the group consisting of polylactic acids, polyvinyl alcohols, polyethylene oxides, polyglycolic acid, polyvinylpyrrolidone, polyacrylic acids, carboxy methyl cellulose, peptides, polysaccharides, proteins and combinations thereof. Suitable surfactants may include, but are not limited to, PLA (polylactic acid), PVOH (polyvinyl alcohol), PEO (polyethylene oxide), PGLA (polyglycolic acid), CMC (carboxymethyl cellulose), PVP polyvinylpyrrolidone, PAA polyacrylic acid, aminoacids, peptides, polysaccharides and proteins (e.g., albumin). and mixtures thereof. Virus and other pathogens are more or less attracted to the varying surfactants.

In yet another embodiment the composition is further comprises an inorganic filler selected from the group consisting of silica, nano-clays, carbon black, graphene, glass fibers, and mixtures thereof.

In another embodiment the composition is in the form of free flowing particles.

In another embodiment, the composition comprises a plurality of discrete carbon nanotubes and a plasticizer wherein the discrete carbon nanotubes comprise from about 10 weight percent to about 90 weight percent, preferably 10 weight percent to 40 weight percent, most preferably 10 to 20 weight percent.

In another embodiment is a process to form a composition comprising discrete carbon nanotubes in a plasticizer? comprising the steps of: a) selecting a plurality of discrete carbon nanotubes having an average aspect ratio of from about 10 to about 500, and an oxidative species content total level from about 1 to about 15% by weight, b) suspending the discrete carbon nanotubes in an aqueous medium (water) at a nanotube concentration from about 1% to about 10% by weight to form an aqueous medium/nanotube slurry, c) mixing the carbon nanotube/aqueous medium (e.g., water) slurry with at least one surfactant at a temperature from about 30° C. to about 100° C. for sufficient time that the carbon nanotubes migrate from the water to the plasticizer to form a wet nanotube/plasticizer mixture, e) separating the water from the wet carbon nanotube/plasticizer mixture to form a dry nanotube/plasticizer mixture, and f) removing residual water from the dry nanotube/plasticizer mixture by drying from about 40° C. to about 120° C. to form an anhydrous nanotube/plasticizer mixture.

Another embodiment is the composition of discrete carbon nanotubes in a surfactant further mixed with a least one rubber. The rubber can be natural or synthetic rubbers and is preferably selected from the from the group consisting of natural rubbers, polyisobutylene, polybutadiene and styrene-butadiene rubber, butyl rubber, polyisoprene, styrene-isoprene rubbers, styrene-isoprene rubbers, ethylene, propylene diene rubbers, silicones, polyurethanes, polyester-polyethers, hydrogenated and non-hydrogenated nitrile rubbers, halogen modified elastomers, flouro-elastomers, and combinations thereof.

Another embodiment is the composition of discrete carbon nanotubes in a plasticizer further mixed with at least one thermoplastic polymer or at least one thermoplastic elastomer. The thermoplastic can be selected from but is not limited to acrylics, polyamides, polyethylenes, polystyrenes, polycarbonates, methacrylics, phenols, polypropylene, polyolefins, such as polyolefin plastomers and elastomers, EPDM, and copolymers of ethylene, propylene and functional monomers.

Yet another embodiment is the composition of discrete carbon nanotubes in a surfactant further mixed with at least one thermoset polymer, preferably an epoxy, or a polyurethane. The thermoset polymers can be selected from but is not limited to epoxy, polyurethane, or unsaturated polyester resins.

For a more complete understanding of the present disclosure, and the advantages thereof, reference is now made to the following descriptions describing specific embodiments of the disclosure.

BRIEF DESCRIPTION OF THE FIGURES

FIG. 1 shows relative protein concentrations on surgical masks with and without a layer of nanotubes.

FIG. 2 shows relative protein concentrations on surgical masks with and without a layer of nanotubes.

FIG. 3 shows protein filtering by varying MR(PVA) coating density on polypropylene PPE material (surgical masks).

FIG. 4 shows protein filtering at constant ratios MR to PVA or PVP on polypropylene PPE material (surgical masks).

FIG. 5 shows protein filtering adjusting MR(PVP) ratio; at constant MR concentration on polypropylene PPE material (surgical masks).

DETAILED DESCRIPTION OF THE INVENTION

In the following description, certain details are set forth such as specific quantities, sizes, etc., so as to provide a thorough understanding of the present embodiments disclosed herein. However, it will be evident to those of ordinary skill in the art that the present disclosure may be practiced without such specific details. In many cases, details concerning such considerations and the like have been omitted inasmuch as such details are not necessary to obtain a complete understanding of the present disclosure and are within the skills of persons of ordinary skill in the relevant art.

While most of the terms used herein will be recognizable to those of ordinary skill in the art, it should be understood, however, that when not explicitly defined, terms should be interpreted as adopting a meaning presently accepted by those of ordinary skill in the art. In cases where the construction of a term would render it meaningless or essentially meaningless, the definition should be taken from Webster's Dictionary, 3rd Edition, 2009. Definitions and/or interpretations should not be incorporated from other patent applications, patents, or publications, related or not.

Functionalized carbon nanotubes of the present disclosure generally refer to the chemical modification of any of the carbon nanotube types described hereinabove. Such modifications can involve the nanotube ends, sidewalls, or both. Chemical modifications may include, but are not limited to covalent bonding, ionic bonding, chemisorption, intercalation, surfactant interactions, polymer wrapping, cutting, solvation, and combinations thereof. In some embodiments, the carbon nanotubes may be functionalized before, during and after being exfoliated.

In various embodiments, a plurality of carbon nanotubes is disclosed comprising single wall, double wall or multi wall carbon nanotube fibers having an aspect ratio of from about 10 to about 500, preferably from about 40 to about 200, and an overall (total) oxidation level of from about 1 weight percent to about 15 weight percent, preferably from about 1 weight percent to about 10 weight percent, more preferably from about 1 weight percent to 5 weight percent, more preferably from about 1 weight percent to 3 weight percent. The oxidation level is defined as the amount by weight of oxygenated species covalently bound to the carbon nanotube. The thermogravimetric method for the determination of the percent weight of oxygenated species on the carbon nanotube involves taking about 7-15 mg of the dried oxidized carbon nanotube and heating at 5° C./minute from 100 degrees centigrade to 700 degrees centigrade in a dry nitrogen atmosphere. The percentage weight loss from 200 to 600 degrees centigrade is taken as the percent weight loss of oxygenated species. The oxygenated species can also be quantified using Fourier transform infra-red spectroscopy, FTIR, particularly in the wavelength range 1730-1680 $cm^{-1}$.

The carbon nanotubes can have oxidation species comprising carboxylic acid or derivative carbonyl containing species and are essentially discrete individual nanotubes, not entangled as a mass. Typically, the amount of discrete carbon nanotubes after completing the process of oxidation and shear is by a far a majority (that is, a plurality) and can be as high as 70, 80, 90 or even 99 percent of discrete carbon nanotubes, with the remainder of the tubes still partially entangled in some form. Complete conversion (i.e., 100 percent) of the nanotubes to discrete individualized tubes is most preferred. The derivative carbonyl species can include phenols, ketones, quaternary amines, amides, esters, acyl halogens, monovalent metal salts and the like, and can vary between the inner and outer surfaces of the tubes.

For example, one type of acid can be used to oxidize the tubes exterior surfaces, followed by water washing and the induced shear, thereby breaking and separating the tubes. If desired, the formed discrete tubes, having essentially no (or zero) interior tube wall oxidation can be further oxidized with a different oxidizing agent, or even the same oxidizing agent as that used for the tubes' exterior wall surfaces at a different concentration, resulting in differing amounts—and/or differing types—of interior and surface oxidation.

As-made carbon nanotubes using metal catalysts such as iron, aluminum or cobalt can retain a significant amount of the catalyst associated or entrapped within the carbon nanotube, as much as five weight percent or more. These residual metals can be deleterious in such applications as electronic devices because of enhanced corrosion or can interfere with the vulcanization process in curing elastomer composites. Furthermore, these divalent or multivalent metal ions can associate with carboxylic acid groups on the carbon nanotube and interfere with the discretization of the carbon nanotubes in subsequent dispersion processes. In other embodiments, the oxidized carbon nanotubes comprise a residual metal concentration of less than about 10000 parts per million, ppm, and preferably less than about 5000 parts per million. The metals can be conveniently determined using energy dispersive X-ray spectroscopy or thermogravimetric methods.

The composition of discrete carbon nanotubes in a plasticizer can be used as an additive to a variety of compounds and composites to improve the mechanical properties, thermal and electrical conductivity. An example is as an additive in rubber compounds used to fabricate rubber components in oil field applications such as seals, blowout preventers and drill motors with improved wear resistance, tear strength and thermal conductivity. Another example is as an additive in rubber compounds used to fabricate tires, seals and vibration dampeners. By selecting the appropriate plasticizer the additive has utility in compounding and formulating in thermoplastics, thermosets and composites.

As manufactured carbon nanotubes are in the form of bundles or entangled agglomerates and can be obtained from different sources, such as CNano Technology, Nanocyl, Arkema, and Kumho Petrochemical, to make discrete carbon nanotubes. An acid solution, preferably nitric acid solution at greater than about 60 weight % concentration, more preferably above 65% nitric acid concentration, can be used to prepare the carbon nanotubes. Mixed acid systems (e. g. nitric and sulfuric acid) as disclosed in US 2012-0183770 A1 and US 2011-0294013 A1, the disclosures of which are incorporated herein by reference, can be used to produce discrete, oxidized carbon nanotubes from as-made bundled or entangled carbon nanotubes.

General Process to Produce Discrete Carbon Nanotubes Having Targeted Oxidation

A mixture of 0.5% to 5% carbon nanotubes, preferably 3%, by weight is prepared with CNano grade Flotube 9000 carbon nanotubes and 65% nitric acid. While stirring, the acid and carbon nanotube mixture is heated to 70 to 90° C. for 2 to 4 hours. The formed oxidized carbon nanotubes are then isolated from the acid mixture. Several methods can be used to isolate the oxidized carbon nanotubes, including but not limited to centrifugation, filtration, mechanical expression, decanting and other solid-liquid separation techniques. The residual acid is then removed by washing the oxidized carbon nanotubes with an aqueous medium such as water, preferably deionized water, to a pH of 3 to 4. The carbon nanotubes are then suspended in water at a concentration of 0.5% to 4%, preferably 1.5% by weight. The solution is subjected to intensely disruptive forces generated by shear (turbulent) and/or cavitation with process equipment capable of producing energy densities of 106 to 108 Joules/$m^3$. Equipment that meet this specification includes but is not limited to ultrasonicators, cavitators, mechanical homogenizers, pressure homogenizers and microfluidizers (Table 1). One such homogenizer is shown in U.S. Pat. No. 756,953, the disclosure of which is incorporated herein by reference. After shear processing, the oxidized carbon nanotubes are discrete and individualized carbon nanotubes. Typically, based on a given starting amount of entangled as-received and as-made carbon nanotubes, a plurality of discrete oxidized carbon nanotubes results from this process, preferably at least about 60%, more preferably at least about 75%, most preferably at least about 95% and as high as 100%, with the minority of the tubes, usually the vast minority of the tubes remaining entangled, or not fully individualized. As used herein, "plurality" means more than any other as is used commonly with respect to election results. Thus, a "plurality" of discrete carbon nanotubes in a given compositions means that there are more nanotubes that are discrete, e.g., individualized and not bundled, within the composition than carbon nanotubes that are not discrete within the composition.

Another illustrative process for producing discrete carbon nanotubes follows: A mixture of 0.5% to 5% carbon nanotubes, preferably 3%, by weight is prepared with CNano Flotube 9000 grade carbon nanotubes and an acid mixture that consists of 3 parts by weight of sulfuric acid (97% sulfuric acid and 3% water) and 1 part by weight of nitric acid (65-70 percent nitric acid). The mixture is held at room temperature while stirring for 3-4 hours. The formed oxidized carbon nanotubes are then isolated from the acid mixture. Several methods can be used to isolate the oxidized carbon nanotubes, including but not limited to centrifugation, filtration, mechanical expression, decanting and other solid-liquid separation techniques. The acid is then removed by washing the oxidized carbon nanotubes with an aqueous medium, such as water, preferably deionized water, to a pH of 3 to 4. The oxidized carbon nanotubes are then suspended in water at a concentration of 0.5% to 4%, preferably 1.5% by weight. The solution is subjected to intensely disruptive forces generated by shear (turbulent) and/or cavitation with process equipment capable of producing energy densities of 106 to 108 Joules/m$^3$. Equipment that meet this specification includes but is not limited to ultrasonicators, cavitators mechanical homogenizers, pressure homogenizers and microfluidizers (Table 1). After shear and/or cavitation processing, the oxidized carbon nanotubes become oxidized, discrete carbon nanotubes. Typically, based on a given starting amount of entangled as-received and as-made carbon nanotubes, a plurality of discrete oxidized carbon nanotubes results from this process, preferably at least about 60%, more preferably at least about 75%, most preferably at least about 95% and as high as 100%, with the minority of the tubes, usually the vast minority of the tubes remaining entangled, or not fully individualized.

Example 1: Entangled Oxidized as MWCNT-3 Hour (oMWCNT-3)

One hundred milliliters of >64% nitric acid is heated to 85° C. To the acid, 3 grams of as-received, multi-walled carbon nanotubes (C9000, CNano Technology) are added. The as-received tubes have the morphology of entangled balls of wool. The mixture of acid and carbon nanotubes are mixed while the solution is kept at 85 degrees for 3 hours and is labeled "oMWCNT-3". At the end of the reaction period, the oMWCNT-3 are filtered to remove the acid and washed with reverse osmosis (RO) water to pH of 3-4. After acid treatment, the carbon nanotubes are still entangled balls. The tubes are dried at 60° C. to constant weight.

Example 2: Entangled Oxidized as MWCNT-6 Hour (oMWCNT-6)

One hundred milliliters of >64% nitric acid is heated to 85 degrees C. To the acid, 3 grams of as-received, multi-walled carbon nanotubes (C9000, CNano Technology) are added. The as-received tubes have the morphology of entangled balls of wool. The mixture of acid and carbon nanotubes are mixed while the solution is kept at 85 degrees for 6 hours and is labeled "oMWCNT-6". At the end of the reaction period, the oMWCNT-6 are filtered to remove the acid and washed with reverse osmosis (RO) water to pH of 3-4. After acid treatment, the carbon nanotubes are still entangled balls. The tubes are dried at 60° C. to constant weight.

Example 3: Discrete Carbon Nanotube-Oxidize Outermost Wall (Out-dMWCNT)

In a vessel, 922 kilograms of 64% nitric acid is heated to 83° C. To the acid, 20 kilograms of as received, multi-walled carbon nanotubes (C9000, CNano Technology) is added. The mixture is mixed and kept at 83° C. for 3 hours. After the 3 hours, the acid is removed by filtration and the carbon nanotubes washed with RO water to pH of 3-4. After acid treatment, the carbon nanotubes are still entangled balls with few open ends. While the outside of the tube is oxidized forming a variety of oxidized species, the inside of the nanotubes have little exposure to acid and therefore little oxidization. The oxidized carbon nanotubes are then suspended in RO water at a concentration of 1.5% by weight. The RO water and oxidized tangled nanotubes solution is subjected to intensely disruptive forces generated by shear (turbulent) and/or cavitation with process equipment capable of producing energy densities of $10^6$ to $10^8$ Joules/m$^3$. The resulting sample is labeled "out-dMWCNT" which represents outer wall oxidized and "d" as discrete. Equipment that meet this shear includes but is not limited to ultrasonicators, cavitators, mechanical homogenizers, pressure homogenizers, and microfluidizers (Table 1). It is believed that the shear and/or cavitation processing detangles and discretizes the oxidized carbon nanotubes through mechanical means that result in tube breaking and opening of the ends due to breakage particularly at defects in the CNT structure which is normally a 6 member carbon rings. Defects happen at places in the tube which are not 6 member carbon rings. As this is done in water, no oxidation occurs in the interior surface of the discrete carbon nanotubes.

Example 4: Discrete Carbon Nanotube-Oxidized Outer and Inner Wall (Out/In-dMWCNT)

To oxidize the interior of the discrete carbon nanotubes, 3 grams of the out-dMWCNT is added to 64% nitric acid heated to 85° C. The solution is mixed and kept at temperature for 3 hours. During this time, the nitric acid oxidizes the interior surface of the carbon nanotubes. At the end of 3 hours, the tubes are filtered to remove the acid and then washed to pH of 3-4 with RO water. This sample is labeled "out/in-dMWCNT" representing both outer and inner wall oxidation and "d" as discrete.

Oxidation of the samples of carbon nanotubes is determined using a thermogravimetric analysis method. In this example, a TA Instruments Q50 Thermogravimetric Analyzer (TGA) is used. Samples of dried carbon nanotubes are ground using a vibration ball mill. Into a tared platinum pan of the TGA, 7-15 mg of ground carbon nanotubes are added. The measurement protocol is as follows. In a nitrogen environment, the temperature is ramped from room temperature up to 100° C. at a rate of 10° C. per minute and held at this temperature for 45 minutes to allow for the removal of residual water. Next the temperature is increased to 700°

C. at a rate of 5° C. per minute. During this process the weight percent change is recorded as a function of temperature and time. All values are normalized for any change associated with residual water removal during the 100° C. isotherm. The percent of oxygen by weight of carbon nanotubes (% Ox) is determined by subtracting the percent weight change at 600° C. from the percent weight change at 200° C.

A comparative table (Table 2 below) shows the levels of oxidation of different batches of carbon nanotubes that have been oxidized either just on the outside (Batch 1, Batch 2, and Batch 3), or on both the outside and inside (Batch 4). Batch 1 (oMWCNT-3 as made in Example 1 above) is a batch of entangled carbon nanotubes that are oxidized on the outside only when the batch is still in an entangled form (Table 2, first column). Batch 2 (oMWCNT-6 as made in Example 2 above) is also a batch of entangled carbon nanotubes that are oxidized on the outside only when the batch is still in an entangled form (Table 2, second column). The average percent oxidation of Batch 1 (2.04% Ox) and Batch 2 (2.06% Ox) are essentially the same. Since the difference between Batch 1 (three hour exposure to acid) and Batch 2 (six hour exposure to acid) is that the carbon nanotubes were exposed to acid for twice as long a time in Batch 2, this indicates that additional exposure to acid does not increase the amount of oxidation on the surface of the carbon nanotubes.

Batch 3 (Out-dMWCNT as made in Example 3 above) is a batch of entangled carbon nanotubes that were oxidized on the outside only when the batch was still in an entangled form (Table 2, third column). Batch 3 was then been made into a discrete batch of carbon nanotubes without any further oxidation. Batch 3 serves as a control sample for the effects compared to Batch 1, Batch 2 and Batch 3. The significant elevation in the average oxidation level in Batch 4 represents the additional oxidation of the carbon nanotubes on their inner surface. Thus, the average oxidation level for Batch 4 (2.39% Ox) is about 20% higher than the average oxidation levels of Batch 3 (1.99% Ox). In Table 2 below, the average value of the oxidation is shown in replicate for the four batches of tubes. The percent oxidation is within the standard deviation for Batch 1, Batch 2 and Batch 3.

TABLE 1

| Homogenizer Type | Flow Regime | Energy Density (J – m$^{-3}$) |
|---|---|---|
| Stirred tanks | turbulent inertial, turbulent viscous, laminar viscous | 10$^3$-10$^6$ |
| Colloid mil | laminar viscous, turbulent viscous | 10$^3$-10$^8$ |
| Toothed - disc disperser | turbulent viscous | 10$^3$-10$^8$ |
| High pressure homogenizer | turbulent inertial, turbulent viscous, cavitation inertial, laminar viscous | 10$^6$-10$^8$ |
| Ultrasonic probe | cavitation inertial | 10$^6$-10$^8$ |
| Ultrasonic jet | cavitation inertial | 10$^6$-10$^8$ |
| Microfluidization | turbulent inertial, turbulent viscous | 10$^6$-10$^8$ |
| Membrane and mircochannel | Injection spontaneous transformation based | Low 10$^3$ |

Excerpted from *Engineering Aspects of Food Emulsification and Homogenization*, ed. M Rayner and P. Dejmek, CRC Press, New York 2015.

TABLE 2

Percent oxidation by weight of carbon nanotubes.

| | Batch 1: oMWCNT-3 % Ox | Batch 2: oMWCNT-6 % Ox | Batch 3: Out-dMWCNT % Ox | Batch 4: Out/In-dMWCNT % Ox | Difference in % Ox (Batch 4 - Batch 3) | *% difference in % Ox (Batch 4 v Batch 3) |
|---|---|---|---|---|---|---|
| | 1.92 | 1.94 | 2.067 | 2.42 | 0.353 | 17% |
| | 2.01 | 2.18 | 1.897 | 2.40 | 0.503 | 26.5% |
| | 2.18 | NM | 2.12 | 2.36 | 0.24 | 11% |
| | 2.05 | NM | 1.85 | NM | n/a | n/a |
| Average | 2.04 | 2.06 | 1.99 | 2.39 | 0.4 | 20% |
| St. Dev. | 0.108 | 0.169 | 0.130 | 0.030 | n/a | n/a |

NM = Not Measured

*% difference between interior and exterior oxidation surfaces (Batch 4 v Batch 3) = (((outside % oxidation) – (inside % oxidation)) ÷ (outside % oxidation)) × 100 on oxidation of rendering entangled carbon nanotubes into discrete nanotubes. Batch 3 shows essentially the same average oxidation level (1.99% Ox) as Batch 1 and Batch 2. Therefore, Batch 3 shows that detangling the carbon nanotubes and making them discrete in water opens the ends of the tubes without oxidizing the interior.

Finally, Batch 4 (Out/In-dMWCNT as made in this Example 4 herein) is a batch of entangled carbon nanotubes that are oxidized on the outside when the batch is still in an entangled form, and then oxidized again after the batch has then been made into a discrete batch of carbon nanotubes (Table 2, fourth column). Because the discrete carbon nanotubes are open-ended, in Batch 4 acid enters the interior of the tubes and oxidizes the inner surface. Batch 4 shows a significantly elevated level of average oxidation (2.39% Ox)

An illustrative process to form a composition comprising discrete carbon nanotubes in a plasticizer is to first select a plurality of discrete carbon nanotubes having an average aspect ratio of from about 10 to about 500, and an oxidative species content total level from about 1 to about 15% by weight. Then the discrete carbon nanotubes are suspended using shear in water at a nanotube concentration from about 1% to about 10% by weight to form the nanotube water slurry. The slurry is then mixed with at least one plasticizer at a temperature from about 30° C. to about 100° C. for sufficient time that the carbon nanotubes migrate from the water to the plasticizer to form a water nanotube/plasticizer mixer. The mixture can comprise from 70% to about 99.9% water. The bulk of the water is separated from the mixture by filtration, decanting or other means of mechanical separation. The filtered material can contain from about 50% to about 10% water. The filtered material is then dried at a temperature from about 40° C. to about 120° C. to form an anhydrous nanotube/plasticizer mixture with less than 3% water, most preferably less than 0.5% water by weight and for some applications 0% water by weight.

Example 5

A concentrate of discrete carbon nanotubes in water with only the exterior wall oxidized as in Example 3 is diluted to a 2% by weight in deionized water. The slurry is heated to 40° C. while stirring with an overhead stirrer at 400 rpm. For every gram of discrete carbon nanotubes, 4 grams of TOTM (trioctyl trimellitate) from Sigma Aldrich is added to the stirring mixture. For 4 hours, the mixture is stirred at 750 rpm and kept at 40° C. During this time, the oil and discrete carbon nanotubes floats to the top, leaving clear water at the bottom. When this occurs, the water is separated from the TOTM/carbon nanotube mixture by filtration. The TOTM and discrete carbon nanotubes are dried in a forced air convection oven at 70° C. until residual water is removed. The result is a flowable powder. The concentration of discrete carbon nanotubes is determined by thermogravimetric means and found to be 20% discrete carbon nanotubes and 80% TOTM.

Example 6

The discrete carbon nanotubes and plasticizer composition of Example 5 comprising 20% discrete carbon nanotubes and 80% TOTM (trioctyle trimellitate) is added at concentrations of 2 parts per hundred resin (phr) and 3 parts per hundred resin (phr) to a nitrile rubber formulation (Table 3). The oil concentration of the compounds is adjusted to compensate for the additional oil from the composition of this invention. The compound is then cured into plaques for testing. Constrained tear testing is performed using an Instron tensiometer. Constrained tear samples are punched out using a die, making a rectangle 1.5 inches by 1 inch by 1 inch with a specimen-centered notch ½ inch long, sliced perpendicular to the longest dimension. The specimen is gripped equal distance from the notch and pulled by the Instron. Shear strain and stress is recorded and the area under the stress-strain curve from strain zero to the final failure is measured. This area is the total tear energy. The results in Table 4 indicate that an increase in tear strength is imparted by the discrete carbon nanotubes.

TABLE 3

| Ingredient | Control | 2 phr dCNT | 3 phr dCNT |
| --- | --- | --- | --- |
| Nitrile Rubber (Nipol 3640S) | 100 | 100 | 100 |
| 20% dCNT in TOTM | 0 | 10 | 15 |
| N774 Carbon Black | 80 | 75 | 75 |
| Polyester sebacate plasticizer (Paraplex G-25) | 15 | 7 | 3 |
| Coumarone Indene Resin (Cumar P25) | 10 | 10 | 10 |
| Stearic Acid | 1 | 1 | 1 |
| Zinc Oxide (Kadox 911) | 5 | 5 | 5 |
| Antioxidant (Vanox CDPA) | 2 | 2 | 2 |
| Antioxidant (Santoflex 6PPD) | 2 | 2 | 2 |
| High molecular fatty acid esters (Struktol WB212) | 2 | 2 | 2 |
| Accelerator DTDM | 2 | 2 | 2 |
| Accelerator (Morfax) | 2.26 | 2.26 | 2.26 |
| Accelerator TMTM | 1 | 1 | 1 |

TABLE 4

| Description | Constrained Tear (psi) |
| --- | --- |
| Control | 482 |
| 2 phr dCNT | 537 |
| 3 phr dCNT | 574 |

Example 7

The discrete carbon nanotubes and plasticizer composition of Example 5 comprising 20% discrete carbon nanotubes and 80% TOTM (trioctyle trimellitate) is added at concentrations 3 parts per hundred resin (phr) to a nitrile rubber formulation (Table 5). The oil concentration of the compound is adjusted to compensate for the additional oil from the composition of this invention so that all formulations have equivalent oil concentrations. A comparative compound is prepared with carbon nanotubes as received (Flotube C9000, CNano) (Table 5). Carbon black content is adjusted so that the measured hardness is the same for the three samples. The Shore A hardness is 67 for the control and 67 for the 3 phr CNT of this invention and 68 for the 3 phr "As is" carbon nanotubes (C9000). The constrained tear is measured as described in Example 6. The discrete carbon nanotubes and oil composition (dCNT) of this invention have higher total tear energy than the entangled carbon nanotubes (C9000) and the control. The tear energy of entangled carbon nanotubes, C9000, is worse than the control. (Table 6)

TABLE 5

| Ingredient | Control | 3 phr dCNT | 3 phr C9000 |
| --- | --- | --- | --- |
| Nitrile Rubber (Nipol 3640S) | 100 | 100 | 100 |
| 20% dCNT in TOTM | 0 | 15 | 0 |
| MWCNT as received (C9000, CNano) | 0 | 0 | 3 |
| N774 Carbon Black | 80 | 75 | 75 |
| Polyester sebacate plasticizer (Paraplex G-25) | 15 | 3 | 15 |
| Coumarone Indene Resin (Cumar P25) | 10 | 10 | 10 |
| Stearic Acid | 1 | 1 | 1 |
| Zinc Oxide (Kadox 911) | 5 | 5 | 5 |
| Antioxidant (Vanox CDPA) | 2 | 2 | 2 |
| Antioxidant (Santoflex 6PPD) | 2 | 2 | 2 |
| High molecular fatty acid esters (Struktol WB212) | 2 | 2 | 2 |
| Accelerator DTDM | 2 | 2 | 2 |
| Accelerator (Morfax) | 2.26 | 2.26 | 2.26 |
| Accelerator TMTM | 1 | 1 | 1 |

TABLE 6

| Description | Constrained Tear (psi) |
| --- | --- |
| Control | 482 |
| 3 phr dCNT | 574 |
| 3 phr C9000 | 394 |

It is known to those practiced in the art that the addition of filler to a rubber compound will increase the viscosity of the compound. Unexpectedly, the addition of discrete carbon nanotube and oil mixture from Example 7 did not increase the viscosity but instead decreased viscosity, while the entangled carbon nanotubes of Example 7 (C9000) increased the viscosity. The viscosity is measured using a Mooney Rheometer at 125° C. The initial viscosity measured is descriptive of the processability of the compound. The compound containing the discrete carbon nanotubes of this invention and described in Example 7 is found to be equal to the control while the compound containing the entangled carbon nanotubes (C9000) is found to be higher than the control (Table 7).

TABLE 7

| Description | Minimum Mooney Viscosity ML(1 + 30) |
|---|---|
| Control | 23.1 |
| 3 phr dCNT | 23.1 |
| 3 phr C9000 | 26.6 |

Disclosed embodiments may also relate to a composition useful for treating and/or remediating contaminated soil, groundwater and/or wastewater by treating, removing, modifying, sequestering, targeting labeling, and/or breaking down at least a portion of any dry cleaning compounds and related compounds such as perchloroethene (PCE), trichloroethene (TCE), 1,2-dichloroethene (DCE), vinyl chloride, and/or ethane. Embodiments may also relate to compounds useful for treating, removing, modifying, sequestering, targeting labeling, and/or breaking down at least a portion of any oils, hazardous or undesirable chemicals, and other contaminants. Disclosed embodiments may comprise a plurality of discrete carbon nanotubes, wherein the discrete carbon nanotubes comprise an interior and exterior surface. Each surface may comprise an interior surface oxidized species content and/or an exterior surface oxidized species content. Embodiments may also comprise at least one degradative or otherwise chemically active molecule that is attached on either the interior or the exterior surface of the plurality of discrete carbon nanotubes. Such embodiments may be used in order to deliver known degrative and/or chemically active molecules to the location of any contaminated soil, groundwater and/or wastewater.

Addition of Payload Molecule

Aqueous solubility of drug substances is an important parameter in pre-formulation studies of a drug product. Several drugs are sparingly water-soluble and pose challenges for formulation and dose administration. Organic solvents or oils and additional surfactants to create dispersions can be used. If the payload molecule is easily dissolved or dispersed in an aqueous media, the filter cake need not be dried. If the payload molecule is not easily dissolved or dispersed in aqueous media, the filter cake is first dried at 80° C. in vacuo to constant weight. The payload molecule in the liquid media at the desired concentration is added to the discrete carbon nanotubes and allowed several hours to equilibrate within the tube cavity. The mixture is then filtered to form a cake, less than about 1 mm thickness, then the bulk of the payload solution not residing within the tubes are removed by high flow rate filtration. The rate of filtration is selected so that little time is allowed for the payload molecules to diffuse from the tube cavity. The filter cake plus payload drug is then subjected to an additional treatment if desired to attach a large molecule such an aqueous solution of a biopolymer, an amino acid, protein or peptide.

Example 8

A calibration curve for the UV absorption of niacin as a function of the concentration of niacin in water was determined. A solution was prepared by mixing 0.0578 grams of discrete functionalized carbon nanotubes of this invention with 0.0134 grams of niacin in 25 ml of water (0.231 grams niacin/gram of carbon nanotube). The tubes were allowed to settle and an aliquot of the fluid above the tubes removed hourly. The UV-vis absorption of this aliquot was measured and the resulting amount of niacin in the solution recorded. The amount of niacin in solution stabilized after 6 hours. A final sample was taken 20 hours after mixing. The difference between the amounts of niacin remaining in the solution and the original amount was determined to be the amount of niacin associated with the discrete functionalized carbon nanotubes. It was found that 0.0746 grams of niacin associated with each gram of carbon nanotubes. The total amount of niacin absorbed by the carbon nanotubes was 0.0043 grams. Assuming an average carbon nanotube length of 1000 nm, external diameter of 12 nm and internal diameter of 5 nm, the available volume within the tube is 0.093 cm3 per gram of carbon nanotubes. Since the density of niacin is 1.473 $g/cm^3$, then the maximum amount of niacin that can fit in the tubes is 0.137 grams. Therefore, the measured absorption of 0.0746 g niacin/g CNT amount could be confined to the interior of the tube.

Example 9

A poly (vinyl alcohol), PVOH, is sufficiently large (30 kDa-70 kDa) that it cannot be absorbed internally in a carbon nanotube. PVOH is used as a surfactant for carbon nanotubes because it associates and wraps the exterior of the carbon nanotube. In this experiment, PVOH was added to a mixture of 0.0535 g of carbon nanotubes and 0.0139 g niacin (0.26 grams niacin to 1 gram carbon nanotubes) in 25 ml water. This was allowed to rest overnight. Using the UV-vis technique of Example 1, the amount of niacin associated with the carbon nanotubes was determined to be 0.0561 grams niacin per gram of carbon nanotubes, less than the 0.0746 grams in example 1. The total amount of niacin absorbed was 0.003 grams.

Calculations were made assuming carbon nanotube length of 1000 nm, external diameter of 12 nm and internal diameter of 5 nm. Given the density of PVOH is 1.1 g/cm3 and the ratio of PVOH to carbon nanotubes was 0.23 to 1, the average layer thickness of PVOH on the carbon nanotube is 0.6 nm. Therefore there is sufficient PVOH to encapsulate the carbon nanotube and displace any niacin on the surface of the tube and the measured amount of 0.0561 grams of niacin per gram of carbon nanotubes is in the interior of the carbon nanotube.

In another example the discrete functionalized carbon nanotubes can be dispersed in a polymeric matrix, for example polyethylene oxide, in the melt or in a solution and the payload molecule added.

TABLE 8

| | Lengths (nm) | | |
|---|---|---|---|
| | Condition 1 | Condition 2 | Condition 3 |
| Mean | 424 | 487 | 721 |
| Standard Error | 25.3 | 34.9 | 50 |
| Median | 407 | 417.0 | 672 |
| Standard Deviation | 177 | 281 | 315 |
| Sample Variance | 31461 | 79108 | 99418 |
| Kurtosis | −0.83 | 1.5 | −0.02 |
| Skewness | 0.03 | 1.2 | 0.64 |
| Range | 650 | 1270.0 | 1364 |

TABLE 8-continued

| | Lengths (nm) | | |
|---|---|---|---|
| | Condition 1 | Condition 2 | Condition 3 |
| Minimum | 85 | 85.0 | 161 |
| Maximum | 735 | 1355 | 1525 |

Condition 1 is an example of a narrow distribution with low mean length. Condition 2 is an example of broad distribution with low mean length. Condition 3 is an example of high mean length and broad distribution.

To determine tube lengths, a sample of tubes is diluted in isopropyl alcohol and sonicated for 30 minutes. It is then deposited onto a silica wafer and images are taken at 15 kV and 20,000× magnification by SEM. Three images are taken at different locations. Utilizing the JEOL software (included with the SEM) a minimum of 2 lines are drawn across on each image and measure the length of tubes that intersect this line.

Skewness is a measure of the asymmetry of a probability distribution. A positive value means the tail on the right side of the distribution histogram is longer than the left side and vice versa. Positive skewness is preferred which indicates means more tubes of long lengths. A value of zero means a relatively even distribution on both sides of the mean value. Kurtosis is the measure of the shape of the distribution curve and is generally relative to a normal distribution. Both skewness and kurtosis are unitless.

The following table shows representative values of discrete carbon nanotubes diameters:

TABLE 9

| Diameter (unrelated to condition above) | | | |
|---|---|---|---|
| Mean diameter (nm*) | | 12.5 | |
| Median diameter (nm) | | 11.5 | |
| Kurtosis | 3.6 | | |
| Skewness | 1.8 | | |
| Calculated aspect ratio (L/D) | 34 | 39 | 58 |

*nm = nanometer

A small sample of the filter cake is dried in vacuum at 100° C. for 4 hours and a thermogravimetric analysis performed at 10° C./min heating rate in nitrogen from 100° C. to 600° C. The amount of oxidized species on the fiber is taken as the weight loss between 200 and 600° C. The dispersion of individual tubes (discrete) is also determined by UV spectroscopy. Water is added to the wet cake to give a 0.5% weight carbon nanotube suspension, then sodium dodecylbenzene sulfonic acid is added at a concentration of 1.5 times the mass of oxidized carbon nanotubes. The solution is sonicated for 30 minutes using a sonicator bath then diluted to a concentration of $2.5 \times 10^{-5}$ g carbon nanotubes/ml. The carbon nanotubes will give a UV absorption at 500 nm of at least 1.2 absorption units.

The improvement in flow processability of the compositions can be determined using a rheometer, for example, utilizing concentric cylinders with a well-defined geometry to measure a fluid's resistance to flow and determine its viscous behavior. While relative rotation of the outer cylinder causes the composition to flow, its resistance to deformation imposes a shear stress on the inner wall of the cup, measured in units of Pa.

Spunbonding of Polyethylene and Polypropylene

Polypropylene is demonstrated in U.S. Pat. No. 4,644,045, incorporated earlier. Patents listed in U.S. Pat. No. 4,644,045 also reference useful patents for making polypropylene fibers which are incorporated by reference as well. A high molecular weight LLDPE copolymer (ethylene/1-octene) having a density of about 0.930 g/cm³ (ASTM D 792) and a MFR (ASTM D1238, Condition 190 C/2.16 kg) of about 18 is dry blended, in particulate form, with a low molecular weight LLDPE copolymer (also ethylene/1-octene) having a density of about 0.930 and a MFR of about 205, with the latter comprising about 10% by wt. of the blend. The blend is fed into an extruder for melt-mixing and conveyed to the spin unit where the polymer melt blend is spun into fine filaments and melt drawn at high velocities typically used in spunbonding. The apparatus is specifically designed for this kind of operation and enables the polymer to undergo rapid draw down (from 600 micrometers to about 20 micrometers filament diameter) and rapid acceleration to about 4000 meters/min. in the space of about 3 meters. Additional details may be found in, for example, Theoretical analysis of the spunbond process and its applications for polypropylene, AIP Conference Proceedings 1779, 120001 (2016) which is incorporated by reference. Polypropylene may have an appropriate melt flow rate for spin bonding. Typically, this is at least about 1, or at least about 20, or at least about 25 up to about 500, or up to about 100, or up to about 5 according to ASTM D1238 2.16 kg 230° C.

The blend is spun at a throughput of about 1.2 g/min/hole, a linear spinning velocity of 4045 m/min, and a polymer melt temperature of about 195° C. The measured titer of the filaments formed under these conditions is about 2.7 denier filament. The physical properties include a tenacity of about 1.49 g/denier and elongation at break of about 163%. Optimized bonded fabric strips exhibit tensiles (tenacity) of about 2400 grams at break (normalized to one ounce per square yard fabric weight). The fabric tenacity is about 52% of the tenacity of the polypropylene tenacity, 4699. In contrast to this the above-described LLDPE, with MFR of 18, when unblended exhibits a linear spinning velocity of only up to 3205 meters/min before excessive fiber breakage occurs and the fiber denier is above 3.

A test on the above polymer blend is performed as follows:

Fibers are collected continuously onto spools using a throughput rate necessary to achieve about the same denier per filament. Polymer temperature stays the same as above. The air gun is not used in this test because of the randomization of the filament splay and the difficulty in separation of individual filaments. After collection of sufficient sample size, the fibers are cut off of the collection spool and cut into 1.5-inch staple fibers. One and one quarter gram samples of these 1.5-inch staple fibers are weighed out and formed into slivers using a Roto Ring (manufactured by Spinlab, Inc.); a sliver is an ordered collection of fibers such that the fiber ends are randomized while the fibers themselves are all paralleled. The structure is about four inches wide by about ten inches long after gently opening the sliver tow. This opened sliver tow is then fed into a Beloit Wheeler calender bonder for thermal tie down of the filaments where pressure and temperature are adjusted for optimal bonding conditions and fabric strength.

The fibers produced from the blend described above are found to have optimum bonding conditions at a top roll (or embossed roll with about 20% land area) temperature of about 114° C. and a bottom roll (smooth roll) temperature of about 117° C. The bonding pressure is found to be optimal at about 700 psig or about 199 pli (pounds per linear inch). After forming a sufficient number of thermally bonded fabrics under the same bonding conditions, a single sample is cut out of each bonded strip which measures 1 by 4 inches.

These samples are individually weighed and then tensiled by use of an Instron tensile tester affixed with a data systems adapter for measuring and recording load and displacement. The mean value of the force required to break this 1 by 4 inch fabric strip, normalized to one ounce per square yard weight, is about 2397 grams bonded fabric tenacity, with a standard deviation of about 8.7%. The percent strain at peak (elongation) of these fabrics average 41% with a standard deviation of 4%.

Masks

A typical inner layer mask material non-woven may have about 25 g polypropylene per square meter or a range of from about 20 to about 60 g polypropylene per square meter. When referring herein to per square meter it is meant per square meter of layer material such as fabric or other material or materials of the mask or personal protective equipment layer. Non-woven fabrics have varying surface area per gram from about 0.2 to about 20 meters square per gram. The instant nanotube coatings on spun-bond fibers may create a surface that attracts proteins in the intricate, tangled fiber of the non-woven structure. The structure of the fiber will often allow more contact with the air flowing through with the higher surface area per gram and the more intricate the fibers are woven. Thus, in some embodiments it is advantageous to coat more of the individual polypropylene fibers with nanotubes. The complexity of the fibers in some cases affect breathability. Thus, it may be advantageous to coat the fibers substantially uniformly with at least 50%, or at least 60%, or at least 80%, or at least 90% up to substantially all the fibers at least partially coated. In some embodiments higher surface area materials with the nanotubes coating may be advantageous.

The loading may vary depending upon the non-woven material, desired results, and application methods. In some embodiments about 0.027 g to 25 g of nanotubes per square meter may be employed. In some embodiments about 2.7 g of nanotubes per square meter may yield up to 94% removal. That is, in this specific embodiment about 10% by weight of the finished fiber comprises nanotubes. In some embodiments the loading is from about 0.027 g to about 25 g per square meter of fabric.

Advantageously, in some embodiments the nanotube coatings do not significantly effect the porosity or breathability of a bulk polypropylene material. Thus, while not wishing to be bound by any particular theory the surface of the polypropylene fibers may be wrapped with the coating.

Additional Mask and Personal Protective Equipment Embodiments

Other personal protective equipment such as masks, gowns, gloves, footies, hats, etc. may be made as described above. Such equipment may protect from nanoparticles such as viruses, droplets, dust, bacteria, germs, smoke, pollutants, chemicals, and more. While the embodiments described throughout may be specifically described with respect to masks the principles apply to the other aforementioned forms of personal equipment as well. Such personal protective equipment in some embodiments may meet or exceed the conventional characteristics and requirements for FDA approved N95 or KN95 respirators and/or surgical masks. N95 and KN95 respirators or masks may have the edges of the respirator or mask configured to form a seal around the nose and mouth. Such respirators or masks generally have fluid resistance, filtration efficiency (particulate filtration efficiency and bacterial filtration efficiency), flammability and biocompatibility. In addition, the respirator or mask may comprise a coronavirus or other pathogen at least partially adhered to the plurality of discrete carbon nanotubes. The mask may include a sensor to indicate the level of coronavirus or other pathogen adhered to the mask or the level or percentage of carbon nanotubes that have adhered coronavirus or other pathogen or the level or percentage of carbon nanotubes that do not have adhered coronavirus or other pathogen. Additional filtering materials such as activated carbon may be employed with or in addition to the nanotubes if desired.

In some embodiments, the personal protective equipment such as masks may have one, two, three, four, five, six or more layers of a fabric. Generally, at least one layer, or at least two layers, or at least three layers, or more comprises an effective amount of a plurality of discrete functionalized nanotubes such as those described above. Often, the one or more layers comprising nanotubes are in one or more layers that are not configured to be directly next to the user's skin. Moreover, in some embodiments it is desired to affix the nanotubes within or on the layer such that they are not removed during normal use. That is, less than 10%, or less than 5%, or less than 1%, or less than 0.5%, or less than 0.1% of the nanotubes are removed during three hours, or one day, or two days, or even three days of routine use. The specific characteristics may vary depending upon the number of layers, type of fabric, and protections desired.

As described above, the layers of fabric may be of a nonwoven or woven fabric. Nonwoven fabric may comprise at least one member from the group consisting of spunbonded fabric, thermally bonded staple fiber, spunlaced fabric, and melt blown fabric. If a polymer is employed in, for example, spunbonded fabric then it may comprise, for example, at least one thermoplastic polymer selected from the group consisting of polypropylene, polyethylene, polyethylene terephthalate, nylon, or a mixture thereof. In some cases cotton or other fabric layers may be employed and in some embodiments, a cotton or polypropylene layer is employed as the layer designed to be adjacent to the skin for comfort reasons.

In another embodiment, a mask may contain three or more layers wherein the inner layer next to the face is a comfort layer comprises of cotton, polypropylene, or similar material that is hypoallergenic and relatively soft to the user. An intermediate meltblown filter and outer non-woven layer may also be employed. The plurality of nanotubes may preferably be disposed on an intermediate or outer non-woven layer.

The size of the mask as manufactured may vary depending upon the characteristics of the intender user or users.

The masks are typically breathable as well as hypoallergenic in some embodiments. Any convenient attachment manner to the user may be employed so long as it is configured to substantially or completely seal the mouth and nose. In some embodiments, elastic or loops of other material are affixed to the mask that are designed to fit relatively comfortably around each ear as seen on conventional surgical masks. Alternatively, the masks may comprise one or more elastic or other bands designed to fit or tie around the back of the head. If desired, the masks and/or attachment mechanism may be made in different sizes to fit users of different size shapes of head and face. Similarly, if desired, an adjustable nose bridge or an expandable, accordion or folded design type mask may be employed so that a single size mask may be adjusted to fit multiple sized faces of users.

The mask size may vary depending upon the configuration, desired user (adult or child), and other characteristics. Typically, the width may be from about 4, or from about 5, or from about 6 up to about, 8, or up to about 7, or up to about 6.5 inches. The height, like the width, may fixed or adjustable and range from about 4 inches to about 7 inches or in the case of adjustable height may have a minimum height of 3.5 to 4.5 inches to a maximum height of 6 to 7 inches.

A given layer may comprise a plurality of discrete nanotubes adhered or admixed with the material of the layer in any convenient manner as described above. Similarly, a given layer of the mask may comprise a surfactant such as those described above with or without nanotubes. In some instances it may be desirable to treat a layer of the mask or the material or materials that will comprise a layer with an appropriate treatment to adhere or better adhere nantotubes, surfactant, or both. In this manner, nanotubes may better adhere to the polypropylene or other material comprising one or more mask layers. Such treatments of the material or layer may include corona treatment, acid treatment, or some other treatment which may facilitate adhesion due to oxidation or other mechanism.

Other treatment of the underlying mask material or layer may also be beneficial depending upon the desired application. For example, a compatibilizer or other substance may be useful for various polyofins. Additionally or alternatively, a crosslinking treatment of a surfactant, nanotubes, or both may be useful before or after coating or making a given mask layer. Similarly, nanotubes may more readily adhere to a given surface or layer material if the nanotubes are heat treated, for example, via microwave (flash or otherwise), infrared, or various combinations thereof.

Additional materials may be added to the surfactant, nanotubes, or both before, during, or after the formation of an effective pathogen controlling mask layer formation. For example, if it desirable to capture water droplets containing a pathogen such as a virus, then it may be desirable to include a hydrophobic material in a layer and/or with the nanotubes and/or surfactant. Similarly, it may be desirable to functionalize the nanotubes to be employed with a hydrophobic material and/or ensure that any surfactant employed is hydrophobic. In this manner, a user of the mask may be protected from aqueous droplets comprising the pathogen such as a virus. The masks are preferably made sterile, e.g., free of pathogens, in any convenient manner before, during, or after they are made. Similarly, the masks may be sterilized and re-used in any convenient manner. Such sterilization methods include, for example, heating (microwave or otherwise), as well as chemical or physical treatments.

As described above, the loading of any carbon nanotube, e.g. MR, containing layer or layers may vary depending upon a number of factors such as type of PPE (msk or other), number of layers, composition of layers, desired results, components, and other factors. In some embodiments about 0.027 g to 25 g of nanotubes per square meter of fabric layer may be employed. That is, at least from about 0.027, or from about 0.05, or from about 0.75, or from about 1.0, or from about 2, or from about 3, or from about 4, or from about 5, or from about 6, or from about 7, or from about 8, or from about 9, or from about 10, or from about 11, or from about 12, or from about 14, or from about 16, or from about 18, or from about 20, up to about 25, or up to about 22, or up to about 20, or up to about 18, or up to about 16, or up to about 14, or up to about 12, or up to about 10, or up to about 8, or up to about 6, or up to about 5, or up to about 4, or up to about 3, or up to about 2, or up to about 1, or up to about 0.75, or up to about 0.5 g of nanotubes per square meter of fabric may be employed.

In some embodiments about 2.7 g of nanotubes per square meter may yield up to 94% removal. That is, in specific embodiments about 10%, or from about 1, or from about 2, or from about 3, or from about 4, or from about 5, or from about 6, or from about 7, or from about 8, or from about 9, or from about 10, or from about 11, or from about 12, or from about 13, or from about 14, or from about 15, or from about 16% by weight up to 25, or up to about 20, or up to about 18, or up to 16, or up to about 14, or up to about 12, or up to 10, or up to about 8% by weight of the finished fiber comprises nanotubes.

Mask Testing

Experiment Description

The studies described here were designed to assess the capability of MR coated with various combinations and proportions of polymers to filter out proteins from an aqueous solution. Round, 126 mm$^2$ areas of polypropylene (PP) material were cut out of the thickest, middle layer of a three-layered, standard surgical mask (PPE). Under microscopy, the morphology of mask materials consisted of polypropylene fibers of heterogenous density, with aggregated nodes of fibers interspersed amid larger areas of fewer, relatively individualized fibers. MR coated on the mask filter samples was combined with the following ratios of molecular species and dispersed by sonication in either 50% ethanol in water or cyclohexane for MR(PIBA):

Summary of MR Coatings and Dispersion Tested

| Molecular Species used for Coating | MR weight/coating volume ratio tested | Disperson |
|---|---|---|
| MR(PEG2k) | 0.55 | 50% EtOH/Water |
| MR(PEG2k) + 0.3% PEO(300k) | 0.56 | 50% EtOH/Water |
| MR(PEG2k) 2× Layers | 0.55 | 50% EtOH/Water |
| MR(PVA) | 0.35 | 50% EtOH/Water |
| MR(PIBA) | 1 | Cyclohexane |

Filter samples were dipped in an excess of MR dispersions at a concentration of 10 mg MR/mL and dried overnight. MR-coated mask samples were then treated with either 1004, of 1 mg/mL bovine serum albumin (BSA) (60 kDa) or Ferritin (770 kDa) proteins. These proteins were allowed to dry on either the uncoated mask material samples or mask samples coated with various combinations of MR and other molecular species described above. Protein was allowed to dry on mask samples for 1 hour at room temperature. Following drying, each of the filter samples was moved to a filtration housing featuring and an inlet and outlet port and which was size-matched for the 126 $mm^2$ round sample material. For each sample tested, 5004, of purified water was run through the filter and the filtrate collected. Any protein not caught by the filters (either uncoated or MR-coated mask material) would flow through the filters and present itself in the filtrate. The concentration of protein in the filtrate was determined used a standard bicinchoninic acid assay (BCA) which measures the optical absorbance of light at 562 nm to quantify total protein concentration within a solution. In the ferritin filtration experiment, the total amount of protein present in the filtrate was compared to the absorbance of 1 mg/mL solution of protein before filtration, as a baseline control.

FIG. 1 Table: "MR + Polymer Coatings on Polypropylene PPE Material (Surgical Mask)"

| | Mean Protein Absorbance Value (AU) | Standard Error |
|---|---|---|
| PP Mask Material | 0.1958 | 0.0164 |
| MR(PEG2k) | 0.0428 | 0.0071 |

Figure 2:
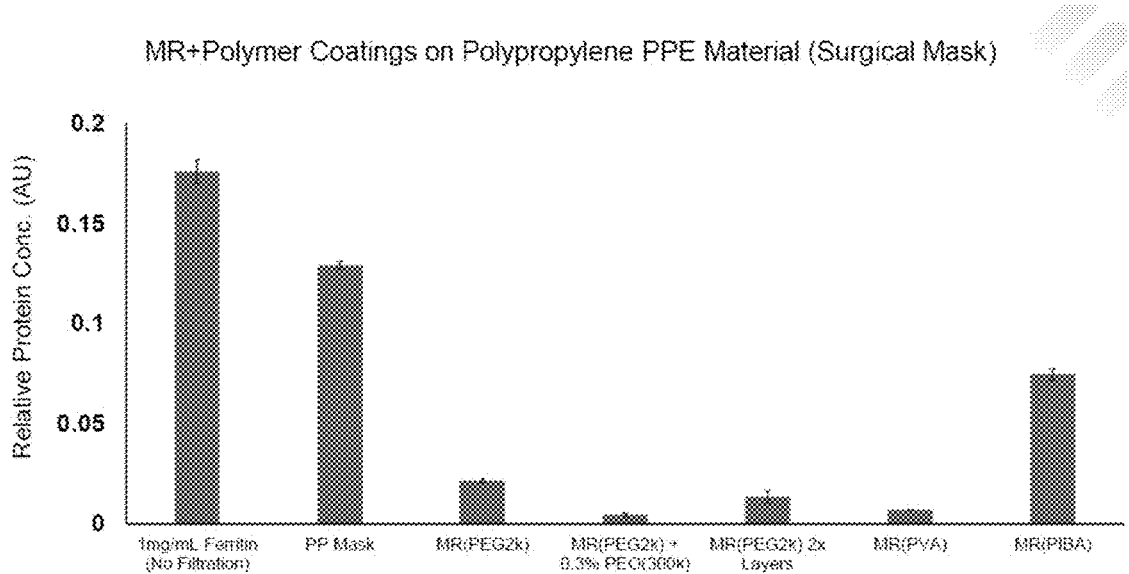

FIG. 2 Table: "MR + Polymer Coatings on Polypropylene PPE Materials (Surgical Mask)"

| | Mean Protein Absorbance Value (AU) | Standard Error |
|---|---|---|
| 1 mg/mL Ferritin (No Filtration) | 0.0901 | 0.0030 |
| PP Mask Material | 0.0652 | 0.0010 |
| MR(PEG2k) | 0.0111 | 0.0005 |
| MR(PEG2k) + 0.3% PEO(300k) | 0.0026 | 0.0005 |
| MR(PEG2k) 2× Layers | 0.0078 | 0.0015 |
| MR(PVA) | 0.0035 | 0.0000 |
| MR(PIBA) | 0.0383 | 0.0015 |

Results

The results of the filtering study indicated that MR coatings could measurably improve filtering efficacy of polypropylene materials tested. In order to test the ability of filters to remove molecular components of various sizes, this study used a relatively large protein, Ferritin (770 kDa) and a smaller entity, BSA (60 kDa). Individual ferritin units are approximately 6 nm in length, but are also capable of complexing iron to form protein cages approximately (12 nm in external diameter) (1). This protein was selected because while it is about 8% the size of a SARS CoV-2 viral particle (2), it can approximate the size and MR-molecular interactions of viral spike proteins which cover the surface of viral particles such as those in SARS CoV-2 (3). The experiments showed that MR coatings improved filtration efficacy of the polypropylene material and that specific combinations of MR and molecular coatings demonstrate better performance than others. For example, MR coated with PIBA improved filtration by 31% relative to the uncoated PP mask material, while MR coated with PVA improved filtration by 69.3% over the uncoated PP mask material. The data showed that adding multiple layers of MR coating may also improve filtration and demonstrated that addition of certain surfactants (such as PEO) to MR dispersions may also improve filtering efficacy. Overall, the ability of MR-coatings to improve filtering efficacy of pathogens such as viruses is strongly governed by MR surface chemistry, as well as density of MR particles coated per unit surface area of filter material.

| Summary Table of Filtering Results for Ferritin, Reporting Filtering Efficacy as a Percentage of Unfiltered Ferritin Solution at 1 mg/mL | Filtering Efficacy of Ferritin 1 mg/mL Solution |
|---|---|
| PP Mask Material | 26.7% |
| MR(PEG2k) | 87.8% |
| MR(PEG2k) + 0.3% PEO(300k) | 97.4% |
| MR(PEG2k) 2× Layers | 92.3% |

-continued

| Summary Table of Filtering Results for Ferritin, Reporting Filtering Efficacy as a Percentage of Unfiltered Ferritin Solution at 1 mg/mL | Filtering Efficacy of Ferritin 1 mg/mL Solution |
|---|---|
| MR(PVA) | 96.0% |
| MR(PIBA) | 57.7% |

Given the smaller size of individual ferritin proteins and their iron-binding complexes relative to viral particles such as SARS CoV-2, the gain in filtering efficacy of MR-coated materials should increase even further when challenged by viral or bacterial pathogens.

Abbreviations

BSA—Bovine Serum Albumin
EtOH—Ethanol
kDa—Kilodalton
MR—Molecular Rebar
MW—Molecular Weight
NM—nanometer
PP—Polypropylene
PPE—Personal Protective Equipment
PEG2k—2000 Molecular Weight Polyethylene Glycol
PEO(300 k)—300,000 Molecular Weight Polyethylene Oxide
PIBA—Polyisobutylene Amine
PVA—Polyvinyl Alcohol

REFERENCES INCORPORATED BY REFERENCE

Theil, Elizabeth C. "Ferritin: the protein nanocage and iron biomineral in health and in disease." *Inorganic chemistry* 52.21 (2013): 12223-12233.

Kim, Jeong-Min, et al. "Identification of Coronavirus Isolated from a Patient in Korea with COVID-19." *Osong Public Health and Research Perspectives* 11.1 (2020): 3.

Wrapp, Daniel, et al. "Cryo-EM structure of the 2019-nCoV spike in the prefusion conformation." *Science* 367.6483 (2020): 1260-1263.

Procedure

Masks comprising, for example, nonwoven fabrics may be coated with from about 0.001 mg discrete carbon nanotubes per $mm^2$ filter to about 0.05 mg discrete carbon nanotubes per $mm^2$ filter. In this example 0.03 mg discrete carbon nanotubes per $mm^2$ filter was used 126 $mm^2$ Filters 10 mg/mL discrete carbon nanotubes ("MR") in 50% EtOH/H2O (Nanopure) except nanotubes (PMA-polyisobutylene amine) in Cyclohexane Coated on single layer (thickest, middle) of surgical mask material (PP) by soaking and dried overnight 100 µL of 1 mg/mL BSA-bovine serum albumin (60 kDa) or Ferritin protein (770 kDa) dropped onto each filter and dried Filtered 500 µL H2O (Nanopure)

Collected filtrate and quantified protein in filtrate by BCA assay

Notes nanotube filters showed superior wetting to mask woven material alone 1 mg/mL BSA spread more evenly across surface of nanotube mask material than uncoated nanotubes (PIBA) mask had dry center area (hydrophobic) but possible flow-through around edges of filter Results Nanotubes +Polymer coatings can be rapidly dried onto mask material and form stable films, do not slough off
  Nanotubes +Polymer coatings shown to significantly improve filtering of polypropylene (PP) surgical mask material
  PP material alone blocked 26% of protein mass from mass through the surgical mask material
  Nanotubes(PVA) blocked 96% of protein from passing through mask material
  2-Layer coating of nanotubes(PEG2k) blocked 97% of protein passing through mask material
  FIG. 1 and FIG. 2 show results.

Additional Filter Examples

Use of a plurality of discrete carbon nanotubes (MR) in filtering of gasses (e.g. breath, air, exhaust) or liquids (e.g. water, body fluids, biological media) and associated pathogens may involve balancing the use of surfactants to disperse nanotubes while potentially avoiding masking a portion to all of the MR surface with sufficient molecular wrapping that the protein-adsorbing surfaces of MR are obscured. Because different coatings, such as surfactant molecules or polymers, may uniquely associate with the MR surface depending on factors such as: (1) concentration or mass ratio of coating molecules relative to units of MR, (2) molecular weight of the coating molecules, (3) chemical interactions of the coating molecule with chemical entities on the MR surface (e.g. graphitic carbon, carbonyl, hydroxyl, carboxylic and amine groups), (4) presence of other molecules competitively interacting with the surface of MR or coating chemistry and/or (5) the identity of the dispersing media (e.g. aqueous environments, polar solvents, non-polar solvents). In practice, this means that there often may exist a useful or optimal range of MR density deposited on the filter, ratio of chemical coating-to-MR, and/or molecular weight of the chemical coating, for each combination of coating chemistry and solvent, used to deposit MR onto a filter material or materials.

General Experimental Description

Preparing MR Dispersions

Molecular Rebar (MR) particles (Molecular Rebar Design, Austin, Tex.) were used to produce dispersions in 50% ethanol/water. Dispersion were produced with various ratios of MR to polyvinyl alcohol (PVA) or polyvinylpyrrolidone (PVP).

Coating PP Mask Material with MR

Non-woven PP surgical mask or other PPE materials were dip-coated in MR dispersions overnight at room temperature. Materials were collected from the coating dispersion and allowed to dry in air. Circular filters were cut from both MR-coated and uncoated PP material by stamping out using a metal die-cutter with a radius of 6.33 mm.

Assessing Protein Filtration

100 µL of 1 mg/mL ferratin solution was loaded onto 3 circular filters for each coating tested and allowed to dry overnight. Following drying, 500 µL of Nanopure water was slowly pumped across each filter, and the protein concentration in the filtrates were measured by standard BCA protein quantification assay, read as absorbance at 562 nm.

Comparing Protein Filtration between Conditions

Protein filtration was assessed from two independent measurements (technical replicates) on each of three coated PP materials (experimental replicates). All filtering efficiencies are relative to unfiltered ferritin protein solution (1 mg/mL) measured independently for each experiment. Statistical error bars in graphs reflect 95% confidence interval (CI).

EXAMPLES

| Protein Filtering by Varying MR(PVA) Coating Densities (Constant 1:0.45 MR:PVA Ratio) on Polypropylene PPE Material (Surgical Mask) | | | |
|---|---|---|---|
| | Mean Protein Absorbance (AU) | 95% CI | % Protein Filtered (vs No Filtration) |
| 1 mg/mL Ferritin (No Filtration) | 0.2235 | 0.0025 | — |
| 0.01% MR(PVA) | 0.1100 | 0.0040 | 50.8% |
| 0.1% MR(PVA) | 0.0850 | 0.0020 | 62.0% |
| 1% MR(PVA) | 0.0375 | 0.0005 | 83.2% |

Figure 3:
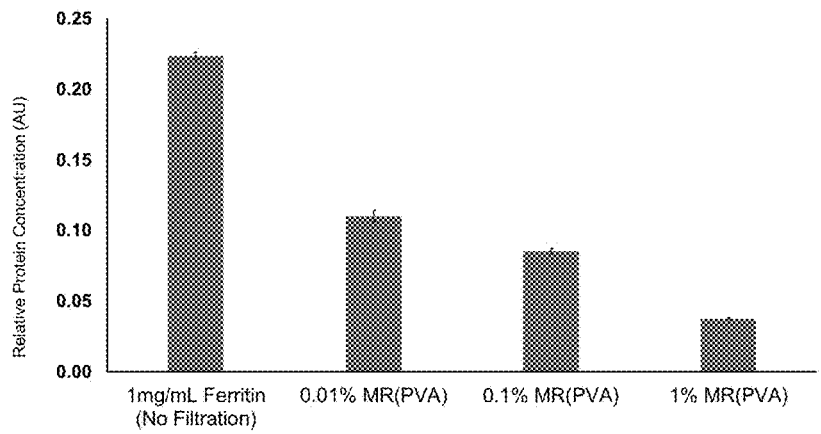

MR(PVA) coating dispersions with increasing concentrations of the particles (m/v %) were used to assess the impact of increasing densities of MR on efficacy of protein capture by coated PP materials. The coating dispersion with the lowest MR concentration demonstrated 51% protein capture relative to the absorbance of the unfiltered ferritin solution. 10-fold increase in MR concentration resulted in 62% protein capture, while the highest MR concentration captured 83% of the protein on the coated PP material. Error bars represent SEM from two measurements. The results are shown in FIG. 3 and above.

| Protein Filtering on PP Filters, at Constant Ratios of MR to PVA or PVP | | | |
|---|---|---|---|
| | Mean Protein Absorbance (AU) | 95% CI | % Protein Filtered (vs No Filtration) |
| 1 mg/mL Ferritin (No Filtration) | 0.2225 | 0.0091 | — |
| Uncoated PP | 0.1418 | 0.0069 | 36.3% |
| 1% MR(PVA) (1:0.45) | 0.0418 | 0.0017 | 81.2% |
| 1% MR(PVP) (1:0.45) | 0.0757 | 0.0079 | 66.0% |

Figure 4:
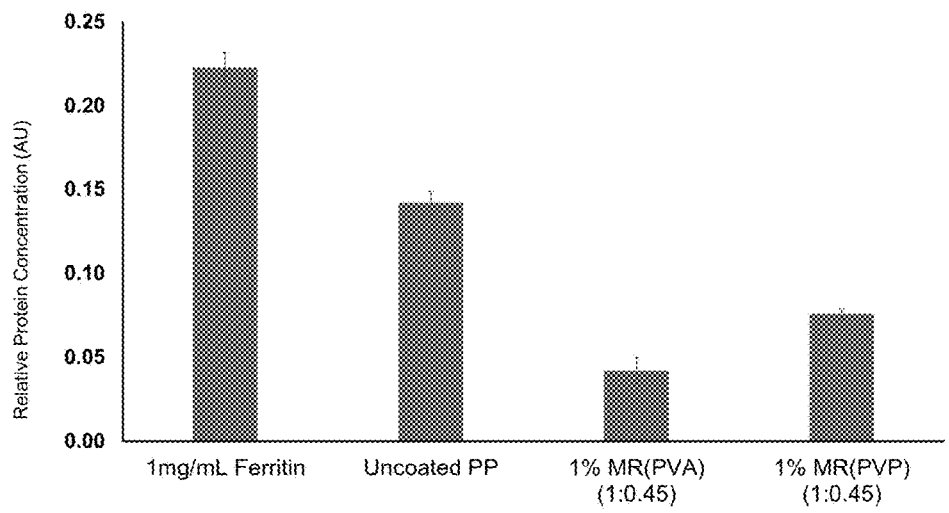
Figure 5:
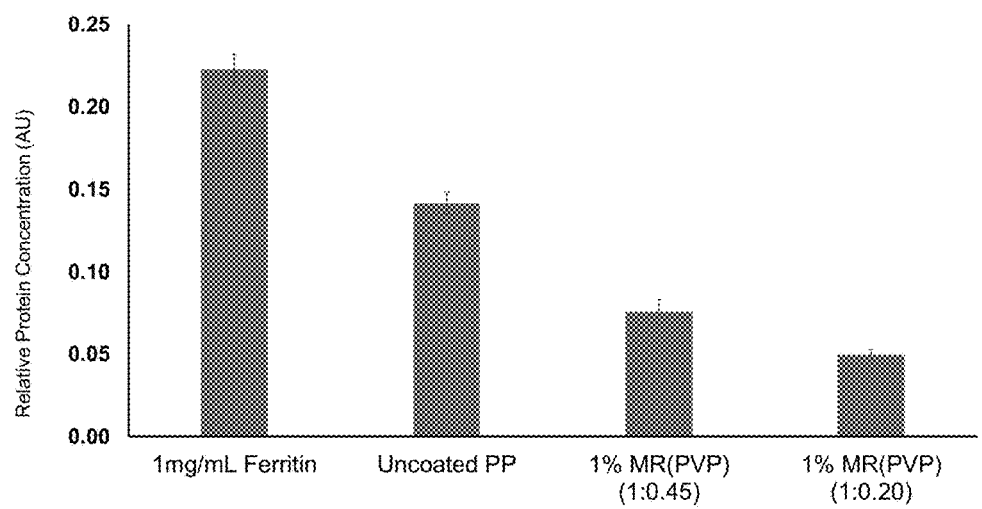

This example studied equal mass ratios of two different coating chemistries on MR and any substantial impact on filtering capability. Dispersions with equal MR-to-coating ratios of either PVA or PVP were prepared and deposited on PP filter material. Both coatings contained the same concentration of MR particles (1% m/v) in the coating dispersions. Despite equal masses of PVA or PVP chemistry on MR, substantially different protein filtering efficacy was observed. MR(PVA) dispersion was the most effective at filtering ferritin protein from the solution, capturing 81% of the protein, compared to 66% by MR(PVP). The uncoated PP fibers captured 36% of the protein from the solution. Thus, even at equivalent mass ratios, the type of coating chemistry used to disperse MR, influences filtration efficacy of MR-coated filters. Filtration efficiency is described relative to absorbance value of unfiltered ferritin solution at 1 mg/mL used in this experiment. Results are shown in FIG. 4 and above.

| Protein Filtering on PP Filters, Adjusting MR(PVP) Ratio; at Constant MR Concentration | | | |
|---|---|---|---|
| | Mean Protein Absorbance (AU) | 95% CI | % Protein Filtered (vs No Filtration) |
| 1 mg/mL Ferritin (No Filtration) | 0.2225 | 0.0091 | — |
| Uncoated PP | 0.1418 | 0.0069 | 36.3% |
| 1% MR(PVP) (1:0.45) | 0.0757 | 0.0079 | 66.0% |
| 1% MR(PVP) (1:0.20) | 0.0497 | 0.0031 | 77.7% |

The altering of the MR-to-coating ratio of a single coating chemistry, while holding constant the concentration of MR in the dispersion measured the impact on the protein filtration capability. 1% MR dispersions (m/v) were prepared by adding PVP in 1:0.45 or 1:0.20 mass ratios relative to MR. Both formulations produced exfoliated dispersions of MR, but more of the MR surface is exposed, e.g, not masked at the lower PVP ratio. The results indicated that the reduced PVP ratio more efficiently filtered the ferritin solution (78%), compared to the higher PVP ratio (66%). The difference between the two was statistically significant, suggesting that surface-masking of MR by a coating agent (e.g. surfactant or polymer) may be an optimization factor. An optimal ratio exists for each coating chemistry, balancing the requirement for dispersion MR with leaving a sufficient surface area on the MR unmasked for protein adsorption. Filtration efficiency is described relative to absorbance value of unfiltered ferritin solution at 1 mg/mL used in this experiment. Results are shown in FIG. 5 and above.

Abbreviations Used

MR—Molecular Rebar (discrete, oxidized multi-wall carbon nanotubes)

NM—nanometer

PP—Polypropylene

PPE—Personal Protective Equipment

PVA—Polyvinyl Alcohol

PVP—Polyvinylpyrrolidone

EMBODIMENTS

Embodiments disclosed include:

A composition comprising a plurality of discrete carbon nanotubes, wherein the discrete carbon nanotubes comprise an interior and exterior surface, each surface comprising an interior surface oxidized species content and an exterior surface oxidized species content, wherein the interior surface oxidized species content differs from the exterior surface oxidized species content by at least 20%, and as high as 100%.

The composition of embodiment 1 wherein the interior surface oxidized species content is less than the exterior surface oxidized species content.

The composition of embodiment 1 wherein the interior surface oxidized species content is up to 3 weight percent relative to carbon nanotube weight, preferably from about 0.01 to about 3 weight percent relative to carbon nanotube weight, more preferably from about 0.01 to about 2, most preferably from about 0.01 to about 1.

The composition of embodiment 1 wherein the exterior surface oxidized species content is from about 1 to about 6 weight percent relative to carbon nanotube weight, preferably from about 1 to about 4, more preferably from about 1 to about 2.

The composition of embodiment 1 wherein the interior and exterior surface oxidized species content totals from about 1 to about 9 weight percent relative to carbon nanotube weight.

A composition comprising a plurality of discrete carbon nanotubes, wherein the discrete carbon nanotubes comprise an interior and exterior surface, each surface comprising an interior surface and an exterior surface oxidized species content, wherein the interior surface oxidized species content comprises from about 0.01 to less than about 1 percent relative to carbon nanotube weight and the exterior surface oxidized species content comprises more than about 1 to about 3 percent relative to carbon nanotube weight.

The composition of embodiment 6 wherein the discrete carbon nanotubes comprise a plurality of open-ended tubes.

The composition of embodiment 6 wherein the plurality of discrete carbon nanotubes comprise a plurality of open-ended tubes.

The composition of embodiment 1 wherein the discrete carbon nanotubes comprise a plurality of open-ended tubes.

Use of the composition of embodiment 1 as an ion transport.

Use of the composition of embodiment 1 as targeting, sequestering and labeling agent in ground water remediation.

A sensor comprising the composition of embodiment 1 or embodiment 6.

A drug delivery or controlled release formulation comprising the composition of embodiment 1 or embodiment 6.

A battery comprising the composition of embodiment 1 or embodiment 6.

A formulation comprising the composition of embodiment 1 or embodiment 6 further comprising an epoxy, a polyurethane, or an elastomer.

The composition of embodiment 1 or embodiment 6 further comprising at least one hydrophobic material in contact with at least one interior surface.

The composition of embodiment 1 or embodiment 6 wherein the inner and outer surface oxidation difference is at least about 0.2 weight percent.

The composition of embodiment 1 or embodiment 6 and at least one plasticizer surfactant, wherein the discrete carbon nanotubes have an aspect ratio of about 10 to about 500, and wherein the carbon nanotubes have an oxidation level of about 1 to 3 percent by weight of carbon nanotubes.

The composition of embodiment 18 wherein the composition comprises from about 10 weight percent to about 90 weight, preferably from about 10 weight percent to about 40 weight percent, discrete carbon nanotubes.

The composition of embodiment 18 wherein the oxygenated species is selected from the group consisting of carboxylic acids, phenols, aldehydes, ketones, ether linkages, and combinations thereof.

The composition of embodiment 18 wherein the total oxygenated species content of the interior surface and exterior surface comprises from about 1% to 15% by weight of the carbon nanotubes.

The composition of embodiment 18, wherein the surfactants is selected from the group consisting of dicarboxylic/tricarboxylic esters, timellitates, adipates, sebacates, maleates, glycols and polyethers, polymeric surfactants, bio-based surfactants, poly vinyl alcohols and mixtures thereof.

The composition of embodiment 18, wherein the surfactant is a process oil selected from the group consisting of naphthenic oils, paraffin oils, paraben oils, aromatic oils, vegetable oils, seed oils, and mixtures thereof.

The composition of embodiment 23 having a viscosity about the same as, or less than, an identical composition comprising the same elements in the same ratios, except the carbon nanotubes are not discrete but are entangled as-manufactured.

The composition of embodiment 18, wherein the surfactant is a water immiscible solvent selected from the group consisting of xylene, pentane, methylethyl ketone, hexane, heptane, ethyl acetate, ethers, dichloromethane, dichloroethane, cyclohexane, chloroform, carbon tetrachloride, butyl acetate butanol, benzene, and mixtures thereof.

The composition of embodiment 18, further comprising an inorganic filler selected from the group consisting of silica, nano-clays, carbon black, graphene, glass fibers, and mixtures thereof.

The composition of embodiment 18 in the form of free flowing particles.

A process to make the composition of embodiment 18, comprising the steps of: a) selecting a plurality of discrete carbon nanotubes having an average aspect ratio of from about 10 to about 500, and an oxidative species content total level from about 1 to about 15% by weight, b) suspending the discrete carbon nanotubes in an aqueous medium at a nanotube concentration from about 1% to about 10% by weight to form an aqueous medium/nanotube slurry, c) mixing the carbon nanotube/aqueous medium slurry with at least one plasticizer at a temperature from about 30° C. to about 100° C. for sufficient time that the carbon nanotubes migrate from the aqueous medium to the plasticizer to form a wet nanotube/plasticizer mixture, e) separating the aqueous medium from the wet carbon nanotube/plasticizer mixture to form a dry nanotube/plasticizer mixture, and f) removing residual aqueous medium from the dry nanotube/plasticizer mixture by drying from about 40° C. to about 120° C. to form an anhydrous nanotube/plasticizer mixture.

The composition of embodiment 18, wherein the composition is further mixed with at least one rubber.

The composition of embodiment 29, wherein the rubber is a natural or synthetic rubber selected from the group consisting of natural rubbers, polyisobutylene, polybutadiene and styrene-butadiene rubber, butyl rubber, polyisoprene, styrene-isoprene rubbers, styrene-isoprene rubbers, ethylene, propylene diene rubbers, silicones, polyurethanes, polyester-polyethers, hydrogenated and non-hydrogenated nitrile rubbers, halogen modified elastomers, fluoro-elastomers, and combinations thereof.

The composition of embodiment 18, wherein the composition further comprises at least one thermoplastic polymer, at least one thermoplastic elastomer, or combinations thereof.

The composition of embodiment 18, wherein the composition further comprises at least one thermoset polymer, preferably epoxy, or polyurethane.

A composition useful for treating groundwater that has been contaminated with dry-cleaning compounds comprising a plurality of discrete carbon nanotubes, wherein the discrete carbon nanotubes comprise an interior and exterior surface, each surface comprising an interior surface oxidized species content and an exterior surface oxidized species content, and at least one degradative molecule that is attached on the interior or exterior surface of the plurality of discrete carbon nanotubes.

A filtration mask comprising a nonwoven comprising polypropylene, a plurality of carbon nanotubes, wherein a plurality of surfaces of the nanotubes is in contact with polyvinyl alcohol, wherein the mask filters and loads with a virus such as SARS CoV-2, and wherein the carbon nanotubes exhibit a varying electrical conductivity before and after loading.

A method of increasing or accelerating cellular growth comprising contacting cells with a plurarilty of discrete carbon nanotubes.

Fabric Embodiments

A woven or nonwoven fabric, each comprising at least one layer having at least one surface, wherein the at least one layer comprises a composition comprising a plurality of discrete carbon nanotubes, wherein the discrete carbon nanotubes comprise an interior and exterior surface, the interior surface comprising an interior surface oxidized species content and the exterior surface comprising an exterior surface oxidized species content, wherein the interior surface oxidized species content differs from the exterior surface oxidized species content by at least 20%, and as high as 100%.

The nonwoven fabric of embodiment 1, wherein the nonwoven fabric comprises at least one member from the group consisting of spunbonded fabric, thermally bonded staple fiber, spunlaced fabric, and melt blown fabric.

The spunbonded fabric of embodiment 2, wherein the fabric comprises at least one thermoplastic polymer selected from the group consisting of polypropylene, polyethylene, polyethylene terephthalate, and nylon.

The spunbonded fabric of embodiment 3 comprising at least two layers.

The spunbonded fabric of embodiment 4, wherein each layer comprises polypropylene.

The spunbonded fabric of embodiment 5 wherein the plurality of discrete carbon nanotubes has a surfactant in contact with at least a portion of a surface of the nanotubes.

The spunbonded fabric of embodiment 5 wherein the plurality of discrete carbon nanotuubes has polyvinyl alcohol in contact with at least a portion of a surface of the nanotubes.

The spunbonded fabric of embodiment 7 wherein the fabric comprises at least 3 layers.

The spunbonded fabric of embodiment 8 wherein the at least one layer comprises at least one interior layer of the fabric, wherein the nanotubes are not in contact with an exterior layer.

A filtration mask comprising the spunbonded fabric of embodiment 9.

A wipe comprising the fabric of embodiment 7.

A filter comprising the spunbonded fabric of embodiment 9.

A method of filtering SARS CoV-2 comprising contacting the SARS CoV-2 with the mask of embodiment 9.

The method of embodiment 13, wherein the interior layer of the fabric is coated with a dispersion comprising the nanotube composition using a spray coating technique.

The composition of embodiment 1, wherein the plurality of discrete carbon nanotubes comprises a plurality of open-ended tubes.

The composition of embodiment 1 wherein the interior surface oxidized species content is less than the exterior surface oxidized species content.

The composition of embodiment 1, wherein the plurality of discrete carbon nanotubes comprises a surfactant that is selected to attract a virus or other pathogen.

Other Uses of Carbon Nanotube Compositions to Control Pathogens Such as SARS COVID-2

The nanotubes described herein (whether functionalized or non-functionalized) and nanotube compositions described herein may be useful in many different manners to reduce, control, absorb, deactivate, detoxify, and/or kill pathogens like viruses e.g., SARS COVID-2, bacteria, mold, fungi, chemical or biological agents etc. That is, using the nanotubes and/or nanotubes in compositions with other components as a platform, pathogens may be reduced, controlled, absorbed, deactivated, detoxified, and/or killed.

The specific nanotube platform employed along with the specific composition and amount of nanotubes may vary depending upon the desired application, the particular pathogen, and the desired effect.

As described above, various woven and non-woven fabrics and the like may be coated with various nanotube compositions for use in, for example, various antiviral applications such as wipes for surfaces comprising pathogens, masks, respirators, air filters for house or auto or airplane or other vehicles, filters for human blood flow such as dialysis or delivered as a drug to filter human lungs, surgical gowns, gloves, aprons, clothing, and/or other personal protective equipment such as may be in a suitable form such as film or semi-breathable films. In doing so it may be useful to coat said article while it is being (spun bonded or otherwise) or after formation with a dispersion of carbon nanotubes such as those described in, for example, U.S. Pat. No. 10,493,626 entitled "Dispersions comprising discrete carbon nanotube fibers" which patent is incorporated herein by reference.

In other embodiments a plurality of carbon nanotubes described above may be employed as a coating on, for example, a surface to potentially capture and/or deactivate a pathogen such as a coronavirus or other pathogen described above. That is ant hard surface could be coated with, for example, a coating like a varnish comprising an appropriate number of nanotubes depending upon the type and number of pathogens expected. In this manner, a device such as cell phone, ipad, laptop, wallet, table, wall, bed, or other surface may be effectively sanitized before a potential user touches it.

Use of MGMR to Treat Viral Infections Such as Coronavirus

MGMR (medical grade MOLECULAR REBAR® brand discrete carbon nanotubes), has the ability to adsorb proteins, anti-bodies, drugs, genetic materials and many biologics. MGMR was shown to adsorb and release vaccine components: adjuvants, antigens and epitopes. When MGMR is used in conjugation with vaccine materials, several mechanisms to suppressing the viral activity are possible. MGMR loaded with vaccine components can shuttle into organs of the immune system: thymus gland, liver, bone marrow, tonsils, lymph nodes and lymphatic system, spleen and blood. Within these tissues, MGMR can infiltrate cells of the immune system: B-cells, Cytotoxic T-Cells, Helper T-Cells, Natural Killer Cells, Monocytes, Dendritic Cells, Neutrophils and Stem Cells and deliver vaccine components to sites on the cellular membrane or within the cellular cytoplasm. In addition to specific vaccine components, MGMR can be loaded with agents for heightening immune activation such as immunoglobulins, immune-cytokines and components of the blood complement cascade.

In addition to acting on the immune system to reduce viral activity, MGMR may engage the virus directly to reduce viral load and slow-down viral replication. The virus itself can be absorbed on MGMR, suppressing the ability of the virus to infect cells and replicate itself. Neutralization of viral activity may increase the window of time for the immune system to mount an effective response to the infection. Another route for reduction of viral load is MGMR removing viruses from the blood and tissues, as during the course of its circulation through the body and eventual clearance via excretion in urine and feces. The combination of these two phenomena may alleviate the effects of the viral infection. Particularly with viruses such as Coronavirus, allowing the body to suppress the effects of the virus on many body functions will allow the body to throw off the effects of the virus.

The high surface-to-volume ratio and ability of MGMR to trap viruses and other pathogens is also exploitable outside the body, where it serves as the basis for disinfection methodology. MGMR-containing filters can be used to scrub viruses and pathogens from circulated blood, in addition to delivery of anti-viral agents. MGMR can also be used to sanitize fluids (e.g. water) and gases (e.g. air) as filtering devices, and MGMR-containing materials such as sponges, gels and textiles can be used as sanitizers/disinfectants by removing viruses and pathogens from solid surfaces.

A third set of possible pathways to control a virus infection such as coronavirus is to adsorb anti-viral agents on the MGMR and release them in blood and tissues. These agents include, for example, Remdesivir, Hydroxychloroquine, Chloroquine and Lopinavir-ritonavir. The agents will be much more effective as the virus is trapped on the MGMR near the anti-viral agent, in effect offer a much higher local concentration of the anti-viral agent allowing it to destroy the virus. With the anti-viral agent on the MGMR, the treatment of the virus can be done at much higher effective concentrations that can be done with just the anti-viral agent. MGMR can be used to control the biological distribution (time and location) as well as dosing of anti-viral agents. Due to the small size and large surface area of MGMR, treatment can be done at the molecular scale and the effects are measured by the number of molecules and MGMR rather than systemic concentration of the drug alone. This will allow from 5×, or 10×, or 50× or more up to 100× or more better effectiveness of the viral agent. This same approach can be used for both bacterial and viral infections by using an appropriate agent for the type of infection.

Functionalized Carbon Nanotubes Such as MGMR

For some applications it may be particularly useful to employ nanotubes that have been functionalized with another chemical moiety. Functionalized carbon nanotubes generally refer to the chemical modification of any of the carbon nanotube types described hereinabove. Such modifications can involve the nanotube ends, sidewalls, or both. Chemical modifications may include, but are not limited to covalent bonding, ionic bonding, chemisorption, intercalation, surfactant interactions, polymer wrapping, cutting, solvation, and combinations thereof. In some embodiments, the carbon nanotubes may be functionalized before, during and after being exfoliated. The carbon nanotubes may have oxidation species comprising of carboxylic acid or derivative carbonyl containing species and are essentially discrete individual fibers, not entangled as a mass. The derivative carbonyl species can include ketones, quaternary amines, amides, esters, acyl halogens, monovalent metal salts and the like.

The particular functionalization may vary depending upon the pathogens to be attacked and the manner of delivery of the anti-pathogen nanotube compositions. For example, in some embodiments it may be desirable to functionalize with antiviral metals or metal compounds or complexes. Alternatively, the nanotubes may simply be mixed with antiviral metals or metal compounds or complexes with, for example, various polymers. Antiviral metal or metal compounds include those metals such as silver, gold, ruthenium, vanadium, copper, titanium, iron (ferrocene), lanthanides and other metal ions.

In other embodiments functionalization or mixing the nanotubes or surfactant/nanotube compositions with an antiviral drug, antigen, or drug/antigen mixture may be desirable. The specific drug or drugs and/or antigens selected will vary depending upon the pathogen to be targeted, application, and desired results. Suitable antigens include, for example, antigenic proteins, peptides (amino acid chains) and polysaccharides (chains of monosaccharides/simple sugars) as well as, lipids and nucleic acids combined with proteins and polysaccharides.

Suitable drugs may include those found in, for example, the 2020 article entitled "A SARS-CoV-2-Human Protein-Protein Interaction Map Reveals Drug Targets and Potential Drug-Repurposing" by David E. Gordon et al. which article is incorporated herein by reference.

In sum, nanotube compositions may be employed in many different forms alone, and/or with surfactants, with antiviral metals, with antigens, and/or with various drugs to control pathogens like viruses e.g., SARS COVID-2, bacteria, mold, fungi, chemical or biological agents etc. The compositions reduce, control, absorb, deactivate, detoxify, and/or kill the pathogens such that a pathogen or pathogens deleterious effects are reduced and/or eliminated.

Representative Specific Embodiments

1. A formulation comprising a plurality of discrete carbon nanotubes wherein the plurality of carbon nanotubes is configured to control or reduce the deleterious effect of one or more pathogens.
2. The formulation of Embodiment 1 wherein the formulation further comprises a surfactant.
3. The formulation of Embodiments 1 or 2 wherein the formulation further comprises an antiviral metal or metal compound wherein the metal is selected from silver, gold, ruthenium, vanadium, copper, titanium, iron (ferrocene), lanthanides, or other metal ions.
4. The formulation of any one of Embodiments 1-3 wherein the formulation further comprises an antigen.
5. The formulation of any one of Embodiments 1-4 wherein the formulation further comprises one or more compounds selected from those in "A SARS-CoV-2-Human Protein-Protein Interaction Map Reveals Drug Targets and Potential Drug-Repurposing" by David E. Gordon et al. which article is incorporated herein by reference.
6. The formulation of any one of Embodiments 1-5 wherein the plurality of carbon nanotubes are functionalized with an antiviral metal, an antigen, one or more compounds selected from those in "A SARS-CoV-2-Human Protein-Protein Interaction Map Reveals Drug Targets and Potential Drug-Repurposing" by David E. Gordon et al. which article is incorporated herein by reference, or a mixture thereof.
7. The formulation of any one of Embodiments 1-6 wherein the pathogen to be reduced or controlled is selected from a virus, bacteria, mold, fungi, a chemical agent, a biological agent, and mixtures thereof.
8. The formulation of any one of Embodiments 1-7 in a form suitable for application to a personal protective equipment.
9. The formulation of Embodiment 8 wherein the personal protective equipment is a mask, gown, glove, face shield, apron, or other clothing.
10. The formulation of any one of Embodiments 1-7 in a form suitable for application or adherence to a pathogen prone surface.
11. The formulation of any one of Embodiments 1-7 in a form suitable for application to an air filter for a building, a vehicle, or machinery.
12. The formulation of any one of Embodiments 1-7 in a form suitable for application to a ventilator.
13. The formulation of any one of Embodiments 1-7 in a form suitable for use in blood dialysis.
14. The formulation of any one of Embodiments 1-7 in a form suitable for use in lungs.
15. The formulation of any one of Embodiments 1-7 in a form suitable for human ingestion.
16. The formulation of any one of Embodiments 1-7 in a form suitable for spraying, dip coating, injecting, or misting an apparatus in need of pathogen control or reduction.

We claim:

1. A mask comprising at least one layer comprising a plurality of discrete carbon nanotubes in an amount of from about 0.5 g to about 2 g of nanotubes per square meter of said layer and at least one surfactant wherein the mask further comprises polypropylene with a melt flow rate of from about 1 to about 500 g/10 min. and wherein the mask further comprises a coronavirus at least partially adhered to the plurality of discrete carbon nanotubes.
2. The mask of claim 1 wherein the mask meets or exceeds May 11, 2020 requirements to be approved as a surgical N95 respirator by the FDA.
3. The mask of claim 1 wherein the mask comprises from 2 to 7 layers wherein a comfort layer is configured to be nearest a user's skin.
4. The mask of claim 1 wherein the mask comprises one or more elastic bands and the surfactant is a crosslinked polyvinylalcohol.
5. The mask of claim 1 wherein the mask comprising the at least one layer comprising the plurality of discrete carbon nanotubes comprises nanotubes in an amount of from about 0.75 g to about 2 g of nanotubes per square meter of said layer.
6. The mask of claim 1 wherein the mask comprising the at least one layer comprising the plurality of discrete carbon nanotubes comprises nanotubes in an amount of from about 1.0 g to about 2 g of nanotubes per square meter of said layer.
7. The mask of claim 1 wherein the mask comprising the at least one layer comprising the plurality of discrete carbon nanotubes comprises nanotubes in an amount of from about 0.75 g to about 1.0 g of nanotubes per square meter of said layer.
8. The mask of claim 1 wherein the mask comprising the at least one layer comprising the plurality of discrete carbon nanotubes comprises nanotubes in an amount of from about 0.5 g to about 1 g of nanotubes per square meter of said layer.
9. The mask of claim 1 wherein the polypropylene has a melt flow rate of from about 20 to about 500 g/10 min. according to ASTM D1238 2.16 kg 230° C.
10. The mask of claim 1 wherein the polypropylene has a melt flow rate of from about 1 to about 100 g/10 min. according to ASTM D1238 2.16 kg 230° C.
11. The mask of claim 1 wherein the polypropylene has a melt flow rate of from about 20 to about 100 g/10 min. according to ASTM D1238 2.16 kg 230° C.

12. The mask of claim 1 wherein the mask comprises from 2 to 4 layers.

13. The mask of claim 1 wherein the at least one surfactant is a polylactic acid, a polyvinyl alcohol, a polyethylene oxide, a polyglycolic acid, polyvinylpyrrolidone, a polyacrylic acid, carboxy methyl cellulose, a peptide, a polysaccharide, or a protein.

14. The mask of claim 1 wherein the at least one surfactant is a crosslinked polyvinylalcohol.

15. The mask of claim 1 wherein the mask further comprises activated carbon.

16. A mask comprising at least one layer comprising a plurality of discrete carbon nanotubes in an amount of from about 2 g to about 25 g of nanotubes per square meter of said layer and at least one surfactant wherein the mask further comprises polypropylene with a melt flow rate of from about 1 to about 500 g/10 min. and wherein the mask further comprises a coronavirus at least partially adhered to the plurality of discrete carbon nanotubes.

17. The mask of claim 16 wherein the at least one surfactant is a crosslinked polyvinylalcohol.

18. The mask of claim 16 wherein the mask meets or exceeds May 11, 2020 requirements to be approved as a surgical N95 respirator by the FDA.

19. The mask of claim 16 wherein the mask comprises from 2 to 7 layers.

* * * * *